US012558540B2

(12) United States Patent　　　(10) Patent No.:　US 12,558,540 B2

Hermosillo et al.　　　　　　　　(45) Date of Patent:　　Feb. 24, 2026

(54) FUNCTIONAL MAGNETIC RESONANCE IMAGING BRAIN MAPPING AND NEUROMODULATION GUIDANCE AND MONITORING BASED THEREON

(71) Applicant: Regents of the University of Minnesota, Minneapolis, MN (US)

(72) Inventors: Robert Jeremiah Matthias Hermosillo, Minneapolis, MN (US); Damien A. Fair, Minneapolis, MN (US); Eric Feczko, Minneapolis, MN (US); Lucille Anne Moore, Minneapolis, MN (US); Óscar Miranda-Domínguez, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 546 days.

(21) Appl. No.: 17/963,009

(22) Filed: Oct. 10, 2022

(65) Prior Publication Data

US 2023/0115330 A1　　Apr. 13, 2023

Related U.S. Application Data

(60) Provisional application No. 63/253,836, filed on Oct. 8, 2021.

(51) Int. Cl.
　　*A61N 1/36*　　　(2006.01)
　　*A61B 5/00*　　　(2006.01)
　　*A61B 5/055*　　　(2006.01)

(52) U.S. Cl.
　　CPC ........ *A61N 1/36025* (2013.01); *A61B 5/0042* (2013.01); *A61B 5/055* (2013.01)

(58) Field of Classification Search
　　CPC .... A61N 1/36025; A61B 5/0042; A61B 5/055
　　See application file for complete search history.

(56) References Cited

U.S. PATENT DOCUMENTS

| | | | |
|---|---|---|---|
| 2015/0119689 A1* | 4/2015 | Pascual-Leone | ...... A61N 2/006 600/407 |
| 2017/0231501 A1* | 8/2017 | Culver | ................. A61B 5/0042 600/425 |

(Continued)

OTHER PUBLICATIONS

Choe, A. S., Jones, C. K., Joel, S. E., Muschelli, J., Belegu, V., Caffo, B. S., Lindquist, M. A., van Zijl, P. C. M., & Pekar, J. J. (2015). Reproducibility and Temporal Structure in Weekly Resting-State fMRI over a Period of 3.5 Years. PloS One, 10(10), e0140134-e0140134. https://doi.org/10.1371/.*

(Continued)

*Primary Examiner* — Stephen R Koziol
*Assistant Examiner* — Michael Kim Maiden
(74) *Attorney, Agent, or Firm* — QUARLES & BRADY LLP

(57)　　　ABSTRACT

Functional networks are mapped for individuals and group populations based on magnetic resonance imaging, and the resulting functional mapping data (e.g., probabilistic maps of functional networks and/or integration zones where multiple functional networks overlap and/or interact) are used to guide or otherwise monitor the delivery of neuromodulation therapies. Individual-specific functional network maps can be generated based on an overlapping template matching that is capable of assigning multiple networks to a given grayordinate.

26 Claims, 16 Drawing Sheets
(9 of 16 Drawing Sheet(s) Filed in Color)

(56) References Cited

U.S. PATENT DOCUMENTS

2019/0090749 A1* 3/2019 Leuthardt .............. G16H 30/40
2021/0170180 A1* 6/2021 Dosenbach ........ A61N 1/36064

OTHER PUBLICATIONS

Friston et al., Movement-related effects in fMRI time-series, Magnetic Resonance in Medicine, 1996, 35(3):346-355.
Friston et al., Nonlinear responses in fMRI: the Balloon model, Volterra kernels, and other hemodynamics, NeuroImage, 2000, 12(4):466-477.
FSL—FSLWIKI, FMRIB Software Library, Retrieved from https://fsl.fmrib.ox.ac.uk/fsl/docs/#/, Version Accessed on Nov. 16, 2023, 1 page.
Github, ABCD-Study, nda-abcd-collection-3165, Retrieved from https://github.com/ABCD-STUDY/nda-abcd-collection-3165, Version Accessed on Nov. 16, 2023, 2 pages.
Github, DCAN-Labs, abcd-hcp-pipeline, Retrieved from https://github.com/DCAN-Labs/abcd-hcp-pipelines, Version Accessed on Nov. 16, 2023, 2 pages.
Github, DCAN-Labs, nda-bids-upload, Retrieved from https://github.com/DCAN-Labs/nda-bids-upload, Version Accessed on Nov. 16, 2023, 2 pages.
Github, Issues, ABCD-STUDY, nda-abcd-collection-3165, Retrieved from https://github.com/ABCD-STUDY/nda-abcd-collection-3165/issues, Version Accessed on Nov. 16, 2023, 2 pages.
Github, MidnightScanClub, MSCcodebase, Retrieved from https://github.com/MidnightScanClub/MSCcodebase, Version Accessed on Nov. 16, 2023, 2 pages.
Glasser et al., Mapping human cortical areas in vivo based on myelin content as revealed by T1-and T2-weighted MRI, Journal of Neuroscience, 2011, 31(32):11597-11616.
Glasser et al., The minimal preprocessing pipelines for the Human Connectome Project, NeuroImage, 2013, 80:105-124.
Glasser et al., A multi-modal parcellation of human cerebral cortex, Nature, 2016, 536(7615):171-178.
Goldstone et al., Sleep disturbance predicts depression symptoms in early adolescence: initial findings from the adolescent brain cognitive development study, Journal of Adolescent Health, 2020, 66(5):567-574.
Gordon et al., Working memory-related changes in functional connectivity persist beyond task disengagement, Human Brain Mapping, 2014, 35(3):1004-1017.
Gordon et al., Generation and evaluation of a cortical area parcellation from resting-state correlations, Cerebral Cortex, 2016, 26(1):288-303.
Gordon et al., Individual variability of the system-level organization of the human brain, Cerebral Cortex, 2017, 27(1):386-399.
Gordon et al., Individual-specific features of brain systems identified with resting state functional correlation, NeuroImage, 2017, 146:918-939.
Gordon et al., Precision functional mapping of individual human brains, Neuron, 2017, 95(4):791-807.
Gordon et al., Three distinct sets of connector hubs integrate human brain function, Cell Reports, 2018, 24(7):1687-1695.
Gorgolewski et al., A high resolution 7-Tesla resting-state fMRI test-retest dataset with cognitive and physiological measures, Scientific Data, 2015, 2(1):1-13.
Gorgolewski et al., BIDS apps: Improving ease of use, accessibility, and reproducibility of neuroimaging data analysis methods, PLoS Computation Biology, 2017, 13(3):e1005209, pp. 1-16.
Gratton et al., Distinct stages of moment-to-moment processing in the cinguloopercular and frontoparietal networks, Cerebral Cortex, 2017, 27(3):2403-2417.
Gratton et al., Control networks and hubs, Psychophysiology, 2018, 55(3):e13032, pp. 1-28.
Gratton et al., Functional brain networks are dominated by stable group and individual factors, not cognitive or daily variation, Neuron, 2018, 98(2):439-452.

Grattton et al., Defining individual-specific functional neuroanatomy for precision psychiatry, Biological Psychiatry, 2020, 88(1):28-39.
Greene et al., Integrative and network-specific connectivity of the basal ganglia and thalamus defined in individuals, Neuron, 2020, 105(4):742-758.
Guerrero et al., Screen time and problem behaviors in children: exploring the mediating role of sleep duration, International Journal of Behavioral Nutrition and Physical Activity, 2019, 16(105):1-10.
Harrison et al., Large-scale probabilistic functional modes from resting state fMRI, NeuroImage, 2015, 109:217-231.
Hermosillo et al., Polygenic risk score-derived subcortical connectivity mediates attention-deficit/hyperactivity disorder diagnosi, Biological Psychiatry: Cognitive Neuroscience and Neuroimaging, 2020, 5(3):330-341.
Huth et al., Natural speech reveals the semantic maps that tile human cerebral cortex, Nature, 2016, 532 (7600):453-458.
Janiri et al., Risk and protective factors for childhood suicidality: a US population-based study, The Lancet Psychiatry, 2020, 7(4):317-326.
Ji et al., Mapping the human brain's cortical-subcortical functional network organization, NeuroImage, 2019, 185:35-57.
Kanwisher et al., The fusiform face area: a module in human extrastriate cortex specialized for face perception, Journal of Neuroscience, 1997, 17(11):4302-4311.
Karcher et al., Resting-state functional connectivity and psychotic-like experiences in childhood: results from the adolescent brain cognitive development study, Biological Psychiatry, 2019, 86(1):7-15.
Kelly et al., Development of anterior cingulate functional connectivity from late childhood to early adulthood, Cerebral Cortex, 2009, 19(3):640-657.
Keuken et al., A probabilistic atlas of the basal ganglia using 7 T MRI, Data in Brief, 2015, 4:577-582.
Klein et al., 101 labeled brain images and a consistent human cortical labeling protocol, Frontiers in Neuroscience, 2012, 6(171):1-12.
Kong et al., Spatial topography of individual-specific cortical networks predicts human cognition, personality, and emotion, Cerebral Cortex, 2019, 29(6):2533-2551.
Kong et al., Individual-specific areal-level parcellations improve functional connectivity prediction of behavior, Cerebral Cortex, 2021, 31(10):4477-4500.
Lancaster et al., A modality-independent approach to spatial normalization of tomographic images of the human brain, Human Brain Mapping, 1995, 3(3):209-223.
Laumann et al., Functional system and areal organization of a highly sampled individual human brain, Neuron, 2015, 87(3):657-670.
Lee et al., Learning the parts of objects by non-negative matrix factorization, Nature, 1999, 401(6755):788-791.
Li et al., Large-scale sparse functional networks from resting state fMRI, NeuroImage, 2017, 156:1-13.
Luciana et al., Adolescent neurocognitive development and impacts of substance use: Overview of the adolescent brain cognitive development (ABCD) baseline neurocognition battery, Developmental Cognitive Neuroscience, 2018, 32:67-79.
Lynch et al., Precision inhibitory stimulation of individual-specific cortical hubs disrupts information processing in humans, bioRxiv preprint doi: https://doi.org/10.1101/254417, 2018, 20 pages.
Mapequation, Multilevel Community Detection with Infomap, Retrieved from https://www.mapequation.org/, Copyright 2020 mathequation.org, 2 pages.
Marek et al., Spatial and temporal organization of the individual human cerebellum, Neuron, 2018, 100(4):977-993.
Marek et al., Identifying reproducible individual differences in childhood functional brain networks: An ABCD study, Developmental Cognitive Neuroscience, 2019, 40:100706, pp. 1-14.
Marek et al., Towards reproducible brain-wide association studies, bioRxiv preprint doi: https://doi.org/10.1101/2020.08.21.257758, 2020, 40 pages.
Marshall et al., Association of lead-exposure risk and family income with childhood brain outcomes, Nature Medicine, 2020, 26(1):91-97.

(56)        References Cited

OTHER PUBLICATIONS

Mathworks, Matlab for Artificial Intelligence, Retrieved from https://www.mathworks.com/, Version Accessed on Nov. 16, 2023, 5 pages.

Mazziotta et al., A probabilistic atlas of the human brain: theory and rationale for its development, NeuroImage, 1995, 2(2):89-101.

Mazziotta et al., A four-dimensional probabilistic atlas of the human brain, Journal of the American Medical Informatics Association, 2001, 8(5):401-430.

Miezin et al., Characterizing the hemodynamic response: effects of presentation rate, sampling procedure, and the possibility of ordering brain activity based on relative timing, NeuroImage, 2000, 11(6):735-759 [In Two Parts Due to File Size].

Miranda-Dominguez et al., Connectotyping: model based fingerprinting of the functional connectome, PloS One, 2014, 9(11):e111048, pp. 1-16.

Mueller et al., Individual variability in functional connectivity architecture of the human brain, Neuron, 2013, 77(3):586-595.

Neta et al., Spatial and temporal characteristics of error-related activity in the human brain, Journal of Neuroscience, 2015, 35(1):253-266.

Newton et al., Improving measurement of functional connectivity through decreasing partial vol. effects at 7 T, NeuroImage, 2012, 59(3):2511-2517.

Noble et al., Influences on the test-retest reliability of functional connectivity MRI and its relationship with behavioral utility, Cerebral Cortex, 2017, 27(11):5415-5429.

Öngür et al., The organization of networks within the orbital and medial prefrontal cortex of rats, monkeys and human, Cerebral Cortex, 2000, 10(3):206-219 [In Three Parts Due to File Size].

Openfmri, The Midnight Scan Club (MSC) Dataset, Retrieved from https://www.openfmri.org/dataset/ds000224/, Version Accessed on Nov. 16, 2023, 6 pages.

Osfhome, ABCD-Bids Community Collection (ABCC), Contributors: Feczko et al., Retrieved from https://osf.io/psv5m/, Version Accessed on Nov. 16, 2023, 4 pages.

Pagliaccio et al., Brain volume abnormalities in youth at high risk for depression: adolescent brain and cognitive development study, Journal of the American Academy of Child & Adolescent Psychiatry, 2020, 59(10):1178-1188.

Pauli et al., A high-resolution probabilistic in vivo atlas of human subcortical brain nuclei, Scientific Data, 2018, 5(1):180063, pp. 1-13.

Poldrack et al., Long-term neural and physiological phenotyping of a single human, Nature Communications, 2015, 6(1):8885, pp. 1-15.

Power et al., Functional network organization of the human brain, Neuron, 2011, 72(4): 665-678.

Power et al., Spurious but systematic correlations in functional connectivity MRI networks arise from subject motion, NeuroImage, 2012, 59(3):2142-2154.

Power et al., Steps toward optimizing motion artifact removal in functional connectivity MRI; a reply to Carp, NeuroImage, 2012, 76:10-1016.

Power et al., Control-related systems in the human brain, Current Opinion in Neurobiology, 2013, 23(2):223-228.

Power et al., Evidence for hubs in human functional brain networks, Neuron, 2013, 79(4):798-813.

Power et al., Methods to detect, characterize, and remove motion artifact in resting state fMRI, NeuroImage, 2014, 84:320-341.

Rajkowska et al., Cytoarchitectonic definition of prefrontal areas in the normal human cortex: II. Variability in locations of areas 9 and 46 and relationship to the Talairach Coordinate System, Cerebral Cortex, 1995, 5(4):323-337.

Rosvall et al., An information-theoretic framework for resolving community structure in complex networks, Proceedings of the National Academy of Sciences, 2007, 104(18):7327-7331.

Rosvall et al., Maps of random walks on complex networks reveal community structure, Proceedings of the National Academy of Sciences, 2008, 105(4):1118-1123.

Rosvall et al., The Map Equation, arXiv preprint arXiv:0906. 1405v2, 2009, 9 pages.

Schaefer et al., Local-global parcellation of the human cerebral cortex from intrinsic functional connectivity MRI, Cerebral Cortex, 2018, 28(9):3095-3114.

Scheinost et al., Fluctuations in global brain activity are associated with changes in whole-brain connectivity of functional networks, IEEE Transactions on Biomedical Engineering, 2016, 63(12):2540-2549.

Seitzman et al., Trait-like variants in human functional brain networks, Proceedings of the National Academy of Sciences, 2019, 116(45):22851-22861.

Seitzman et al., A set of functionally-defined brain regions with improved representation of the subcortex and cerebellum, NeuroImage, 2020, 206:116290, pp. 1-17.

Siegel et al., Data quality influences observed links between functional connectivity and behavior, Cerebral Cortex, 2017, 27(9):4492-4502.

Silasi et al., Stroke and the connectome: how connectivity guides therapeutic intervention, Neuron, 2014, 83(6):1354-1368.

Smith et al., Statistical challenges in "big data" human neuroimaging, Neuron, 2018, 97(2):263-268.

Sporns et al., Identification and classification of hubs in brain networks, PLoS One, 2007, 2(10):e1049, pp. 1-14.

Stein et al., Multisensory integration: current issues from the perspective of the single neuron, Nature Reviews Neuroscience, 2008, 9(4):255-266.

Sylvester et al., Individual-specific functional connectivity of the amygdala: A substrate for precision psychiatry, Proceedings of the National Academy of Sciences, 2020, 117(7):3808-3818.

Szucs et al., Empirical assessment of published effect sizes and power in the recent cognitive neuroscience and psychology literature, PLoS Biology, 2017, 15(3):e2000797, pp. 1-18.

The National Institute of Mental Health Data Archive, Nimh Data Archive—NDA Home Page, Retrieved from https://nda.nih.gov/, Version Accessed on Nov. 16, 2023, 5 pages.

Thompson et al., Detection and mapping of abnormal brain structure with a probabilistic atlas of cortical surfaces, Journal of Computer Assisted Tomography, 1997, 21(4):567-581.

Thompson et al., The structure of cognition in 9 and 10 year-old children and associations with problem behaviors: Findings from the ABCD study's baseline neurocognitive battery, Developmental Cognitive Neuroscience, 2019, 36:100606, pp. 1-2.

Tustison et al., N4ITK: improved N3 bias correction, IEEE Transactions on Medical Imaging, 2010, 29(6):1310-1320.

Tyszka et al., In vivo delineation of subdivisions of the human amygdaloid complex in a high-resolution group template, Human Brain Mapping, 2016, 37(11):3979-3998.

University of Minnesota, Office of Academic Clinical Affairs, Masonic Institute for the Developing Brain, MIDB Precision Brain Atlas, Retrieved from https://midbatlas.io/, Version Accessed on Nov. 16, 2023, 2 pages.

Van Den Heuvel et al., Rich-club organization of the human connectome, Journal of Neuroscience, 2011, 31(44):15775-15786.

Van Den Heuvel et al., Network hubs in the human brain, Trends in Cognitive Sciences, 2013, 17(12):683-696.

Van Den Heuvel et al., A cross-disorder connectome landscape of brain dysconnectivity, Nature Reviews Neuroscience, 2019, 20(7):435-446.

Van Essen et al., A population-average, landmark-and surface-based (PALS) atlas of human cerebral cortex, NeuroImage, 2005, 38(3):635-662.

Van Essen et al., The Human Connectome Project: a data acquisition perspective, NeuroImage, 2012, 62(4):2222-2231.

Vesia et al., Specialization of reach function in human posterior parietal cortex, Experimental Brain Research, 2012, 221:1-18.

Volkow et al., The conception of the ABCD study: From substance use to a broad NIH collaboration, Developmental Cognitive Neuroscience, 2018, 32:4-7.

Wang et al., Parcellating cortical functional networks in individuals, Nature Neuroscience, 2015, 18(12):1853-1860.

Wang et al., Probabilistic maps of visual topography in human cortex, Cerebral Cortex, 2015, 25(10):3911-3931.

(56)     References Cited

OTHER PUBLICATIONS

Weigand et al., Prospective validation that subgenual connectivity predicts antidepressant efficacy of transcranial magnetic stimulation sites, Biological Psychiatry, 2018, 84(1):28-37.

Xing et al., Probabilistic MRI brain anatomical atlases based on 1,000 Chinese subjects, PLoS One, 2013, 8(1):e50939, pp. 1-6.

Yang et al., Overlapping community detection at scale: a nonnegative matrix factorization approach, Proceedings of the Sixth ACM International Conference on Web Search and Data Mining, 2013, 10 pages.

Yeo et al., The organization of the human cerebral cortex estimated by intrinsic functional connectivity, Journal of Neurophysiology, 2011, 106:1125-1165.

Zhou et al., Functional connectivity of the caudal anterior cingulate cortex is decreased in autism, PLoS One, 2016, 11(3):e0151879, pp. 1-14.

Adolescent Brain Cognitive Development, The ABCD Study®, Retrieved from https://abcdstudy.org/, Version Accessed on Nov. 16, 2023, 2 pages.

Alexander et al., A new neonatal cortical and subcortical brain atlas: the Melbourne Children's Regional Infant Brain (M-CRIB) atlas, NeuroImage, 2017, 147:841-851.

Alexander et al., Desikan-Killiany-Tourville atlas compatible version of M-CRIB neonatal parcellated whole brain atlas: The M-CRIB 2.0, Frontiers in Neuroscience, 2019, 13(34):1-9.

Alvarado et al., A neural network model of multisensory integration also accounts for unisensory integration in superior colliculus, Brain Research, 2008, 1242:13-23.

Andersen, Multimodal integration for the representation of space in the posterior parietal cortex, Philosophical Transactions of the Royal Society of London. Series B: Biological Sciences, 1997, 352(1360):1421-1428.

Anderson et al., Reproducibility of single-subject functional connectivity measurements, American Journal of Neuroradiology, 2011, 32(3):548-555.

Avants et al., Advanced normalization tools (ANTS), The Insight Journal, 2009, 2(365):1-35.

Bagarinao et al., Identifying the brain's connector hubs at the voxel level using functional connectivity overlap ratio, NeuroImage, 2020, 222:117241, 11 pages.

Bertolero et al., The modular and integrative functional architecture of the human brain, Proceedings of the National Academy of Sciences, 2015, 112(49):E6798-E6807.

Braga et al., Parallel interdigitated distributed networks within the individual estimated by intrinsic functional connectivity, Neuron, 2017, 95(2):457-471.

Braga et al., Parallel distributed networks resolved at high resolution reveal close juxtaposition of distinct regions, Journal of Neurophysiology, 2019, 121(4):1513-1534.

Brain Imaging Data Stucture, Governance and Decision Making, Retrieved from https://bids.neuroimaging.io/collaboration/governance.html, Version Accessed on Nov. 16, 2023, 11 pages.

Buckner et al., Cortical hubs revealed by intrinsic functional connectivity: mapping, assessment of stability, and relation to Alzheimer's disease, The Journal of Neuroscience, 2009, 29(6):1860-1873.

Buckner et al., The evolution of distributed association networks in the human brain, Trends in Cognitive Sciences, 2013, 17(12):648-665.

Carmichael et al., Connectional networks within the orbital and medial prefrontal cortex of macaque monkeys, The Journal of Comparative Neurology, 1996, 371(2):179-207.

Casey et al., The adolescent brain cognitive development (ABCD) study: imaging acquisition across 21 sites, Developmental Cognitive Neuroscience, 2018, 32:43-54.

Cash et al., Subgenual functional connectivity predicts antidepressant treatment response to transcranial magnetic stimulation: independent validation and evaluation of personalization, Biological Psychiatry, 2019, 86(2):e5-e7.

Cash et al., Functional magnetic resonance imaging-guided personalization of transcranial magnetic stimulation treatment for depression, JAMA Psychiatry, 2021, 78(3):337-339.

Cash et al., Personalized connectivity-guided DLPFC-TMS for depression: Advancing computational feasibility, precision and reproducibility, Human Brain Mapping, 2021, 42(13):4155-4172.

Cash et al., Using brain imaging to improve spatial targeting of transcranial magnetic stimulation for depression, Biological Psychiatry, 2021, 90(10):689-700.

Caspers et al., The human inferior parietal cortex: cytoarchitectonic parcellation and interindividual variability, NeuroImage, 2006, 33(2):430-448.

Churchland et al., Perspectives on cognitive neuroscience, Science, 1988, 242(4879):741-745.

Ciric et al., Benchmarking of participant-level confound regression strategies for the control of motion artifact in studies of functional connectivity, NeuroImage, 2017, 154:174-187.

Cole et al., Stanford neuromodulation therapy (SNT): a double-blind randomized controlled trial, American Journal of Psychiatry, 2022, 179(2):132-141.

Collection 3165—ABCD-Bids Community Collection (ABCC), ABCD-Bids Community Collection (ABCC) Documentation Summary, Retrieved from https://collection3165.readthedocs.io/en/stable/, Version Accessed on Nov. 16, 2023, 2 pages.

Connectome Coordination Facility, Using Conenctome Workbench, Retrieved from https://www.humanconnectome.org/software/connectome-workbench, Version Accessed on Nov. 16, 2023, 8 pages.

Connectome Coordination Facility, What is the Connectome Coordination Facility?, Retrieved from https://www.humanconnectome.org/, Version Accessed on Nov. 16, 2023, 12 pages.

Cui et al., Individual variation in functional topography of association networks in youth, Neuron, 2020, 106(2):340-353.

Desikan et al., An automated labeling system for subdividing the human cerebral cortex on MRI scans into gyral based regions of interest, NeuroImage, 2006, 31(3):968-980.

Destrieux et al., Automatic parcellation of human cortical gyri and sulci using standard anatomical nomenclature, NeuroImage, 2010, 53(1):1-15.

Diedrichsen et al., A probabilistic MR atlas of the human cerebellum, NeuroImage, 2009, 46(1):39-46.

Dosenbach et al., Real-time motion analytics during brain MRI improve data quality and reduce costs, NeuroImage, 2017, 161:80-93.

Driver et al., Multisensory interplay reveals crossmodal influences on 'sensory-specific' brain regions, neural responses, and judgments, Neuron, 2008, 57(1):11-23.

Du et al., Group information guided ICA for fMRI data analysis, NeuroImage, 2013, 69:157-197.

Dubis et al., Tasks driven by perceptual information do not recruit sustained BOLD activity in cingulo-opercular regions, Cerebral Cortex, 2016, 26(1):192-201.

Dworetsky et al., Probabilistic mapping of human functional brain networks identifies regions of high group consensus, NeuroImage, 2021, 237:118164, pp. 1-10.

Eickhoff et al., Imaging-based parcellations of the human brain, Nature Reviews Neuroscience, 2018, 19(11):672-686.

Elliott et al., General functional connectivity: Shared features of resting-state and task fMRI drive reliable and heritable individual differences in functional brain networks, NeuroImage, 2019, 189:516-532.

Evans et al., 3D statistical neuroanatomical models from 305 MRI vols. 1993 IEEE Conference Record Nuclear Science Symposium and Medical Imaging Conference, IEEE, 1993, pp. 1813-1817.

Fair et al., Functional brain networks develop from a "local to distributed" organization, PLoS Computational Biology, 2009, 5(5):e1000381, pp. 1-14.

Fair et al., Correction of respiratory artifacts in MRI head motion estimates, NeuroImage, 2020, 208:116400, pp. 1-17.

Fan et al., The human brainnetome atlas: a new brain atlas based on connectional architecture, Cerebral Cortex, 2016, 26(8):3508-3526.

Faraone et al., Attention-deficit/hyperactivity disorder, Nature Reviews, Disease Primers, 2015, 1:15020, pp. 1-23.

(56)            References Cited

OTHER PUBLICATIONS

Feczko et al., Adolescent brain cognitive development (ABCD) community MRI collection and utilities, bioRxiv preprint doi: https://doi.org/10.1101/2021.07.09.451638, 2021, 33 pages.

Felleman et al., Distributed hierarchical processing in the primate cerebral cortex, Cerebral Cortex, 1991, 1(1):1-47, Jun. 9, 2025.

Finn et al., Functional connectome fingerprinting: identifying individuals using patterns of brain connectivity, Nature Neuroscience, 2015, 18(11):1664-1671.

Fonov et al., Unbiased average age-appropriate atlases for pediatric studies, NeuroImage, 2011, 54(1):313-327.

Fox et al., Efficacy of transcranial magnetic stimulation targets for depression is related to intrinsic functional connectivity with the subgenual cingulate, Biological Psychiatry, 2012, 72(7):595-603.

Fox et al., Measuring and manipulating brain connectivity with resting state functional connectivity magnetic resonance imaging (fcMRI) and transcranial magnetic stimulation (TMS), NeuroImage, 2012, 62(4):2232-2243.

Freesurfer, FreeSurfer Software Suite, Retrieved from https://surfer.nmr.mgh.harvard.edu/, Version Accessed on Nov. 16, 2023, 2 pages.

* cited by examiner

400

402
Access Individual-Specific
Functional Network Map Data

404
Generate Probabilistic Functional Network Atlas(es) Based on
the Individual-Specific Functional Network Map Data 406
Store and/or Display the Probabilistic
Functional Network Atlas(es)

600

602

Access Individual-Specific
Functional Network Map Data

604

Generate Individual-Specific Integration Zone Map(s) Based on
the Individual-Specific Functional Network Map Data

606

Store and/or Display the Individual-
Specific Integration Zone Map(s)

800

Access Individual-Specific
Integration Zone Map Data
802

Generate Probabilistic Integration Zone Map(s) Based on the
Individual-Specific Integration Zone Map Data
804

Store and/or Display the Probabilistic
Integration Zone Map(s)
806

FUNCTIONAL MAGNETIC RESONANCE IMAGING BRAIN MAPPING AND NEUROMODULATION GUIDANCE AND MONITORING BASED THEREON

STATEMENT REGARDING FEDERALLY SPONSORED RESEARCH

This invention was made with government support under MH096773, MH115357, MH091238, MH118370, awarded by the National Institutes of Health. The government has certain rights in the invention.

BACKGROUND

Since the wide-spread adoption of non-invasive brain stimulation such as transcranial direct current/alternating-current stimulation ("TDCS/TACS") and transcranial magnetic stimulation ("TMS"), technologies for non-invasive brain stimulation have quickly outpaced techniques for neuronavigation. In TMS, early studies relied on a fixed distance from the motor cortex, which was then followed by an electroencephalography ("EEG") cap positioning system. More recently, the gold standard for TMS uses real-time neuronavigation based on stereotactic image-guided positioning.

In clinical practice, most neuromodulation targeting is done by using relative anatomical distances. Unfortunately, this approach is insensible to individual differences in brain functional topography.

SUMMARY OF THE DISCLOSURE

The present disclosure addresses the aforementioned drawbacks by providing a method for guiding a delivery of neuromodulation to a subject's brain. The method includes accessing a probabilistic functional mapping data with a computer system, where the probabilistic functional mapping data includes at least one of a probabilistic functional network map or a probabilistic integration zone map. One or more target locations are determined in the probabilistic functional mapping data using the computer system, where the one or more target locations indicate locations to which neuromodulation should be delivered. The one or more target locations are then localized relative to the brain of the subject, thereby guiding delivery of the neuromodulation to the one or more target locations.

It is another aspect of the present disclosure to provide a method for generating a functional network map from functional magnetic resonance image data acquired from a subject using an MRI system. The method includes accessing functional magnetic resonance image data with a computer system, where the functional magnetic resonance image data comprise a time-series of images whose voxels depict blood-oxygen-level-dependent (BOLD) signals. Time course signal data are formed for each grayordinate with the computer system, where the time course signal data are formed for each gray ordinate as BOLD signals at the grayordinate measured over the time series of images. A correlation matrix is computed from the time course signal data for each grayordinate using the computer system. Functional network template data are accessed with the computer system, where the functional network template data include functional network templates that are each indicative of grayordinates associated with a different functional network, and similarity values are computed between the correlation matrix and each functional network template in the functional network template data. An individual-specific functional network map is then generated with the computer system using a data-driven approach to assign multiple networks to grayordinates based on the similarity values.

In some aspects, the functional magnetic resonance data were acquired after a neuromodulation therapy was delivered to the subject. In these instances, an efficacy of the neuromodulation therapy can be measured or otherwise monitored by comparing the individual-specific functional network map to a reference functional network map.

The neuromodulation therapy can include a brain stimulation therapy, such as transcranial direct-current stimulation, transcranial alternating-current stimulation, or transcranial magnetic stimulation.

The efficacy of the neuromodulation therapy can be measured by comparing the individual-specific functional network map to the reference functional network map on a brainordinate basis. For instance, the individual-specific functional network map can be compared to the reference functional network map on grayordinate basis. The efficacy of the neuromodulation therapy can also be measured by comparing the individual-specific functional network map to the reference functional network map on a functional network basis.

In some instances, the reference functional network map can include a second individual-specific functional network map generated for the subject before the neuromodulation therapy was delivered to the subject. In some other instances, the reference functional network map includes a second individual-specific functional network map generated for a different subject. In still other instances, the reference functional network map can include a probabilistic functional network map associated with a group of subjects.

In some other aspects, an individual-specific integration zone map is generated with the computer system by determining the functional networks associated with each grayordinate in the individual-specific functional network map and assigning grayordinates in the individual-specific integration zone map to one or more integration zones based on the functional networks associated with each grayordinate. Where the functional magnetic resonance data were acquired after a neuromodulation therapy was delivered to the subject, the efficacy of the neuromodulation therapy can additionally or alternatively be measured or otherwise monitored by comparing the individual-specific integration zone map to a reference integration zone map.

The neuromodulation therapy can include a brain stimulation therapy, such as transcranial direct-current stimulation, transcranial alternating-current stimulation, or transcranial magnetic stimulation.

The efficacy of the neuromodulation therapy can be measured by comparing the individual-specific integration zone map to the reference functional integration zone map on a brainordinate basis. For instance, the individual-specific integration zone map can be compared to the reference integration zone map on grayordinate basis. The efficacy of the neuromodulation therapy can also be measured by comparing the individual-specific integration zone map to the reference integration zone map on an integration zone basis.

In some instances, the reference integration zone map can include a second individual-specific integration zone map generated for the subject before the neuromodulation therapy was delivered to the subject. In some other instances, the reference integration zone map can be a second individual-specific integration zone map generated for a different subject. In still other instances, the reference integration zone map can include a probabilistic integration zone map associated with a group of subjects.

It is still another aspect of the present disclosure to provide a method for generating a probabilistic integration zone map based on functional magnetic resonance image data acquired from a group of subjects using MRI. The method include accessing individual-specific integration zone maps for each subject in the group of subjects using a computer system. The individual-specific integration zone maps indicate grayordinates that are assigned to one or more integration zones for each subject in the group of subjects, where each integration zone is associated with at least two functional networks overlapping at one or more common grayordinates. A probabilistic integration zone map is generated with the computer system by computing a probability for each grayordinate across the group of subjects that the grayordinate is assigned to a particular integration zone. The probabilistic integration zone map can then be stored for later use using the computer system.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
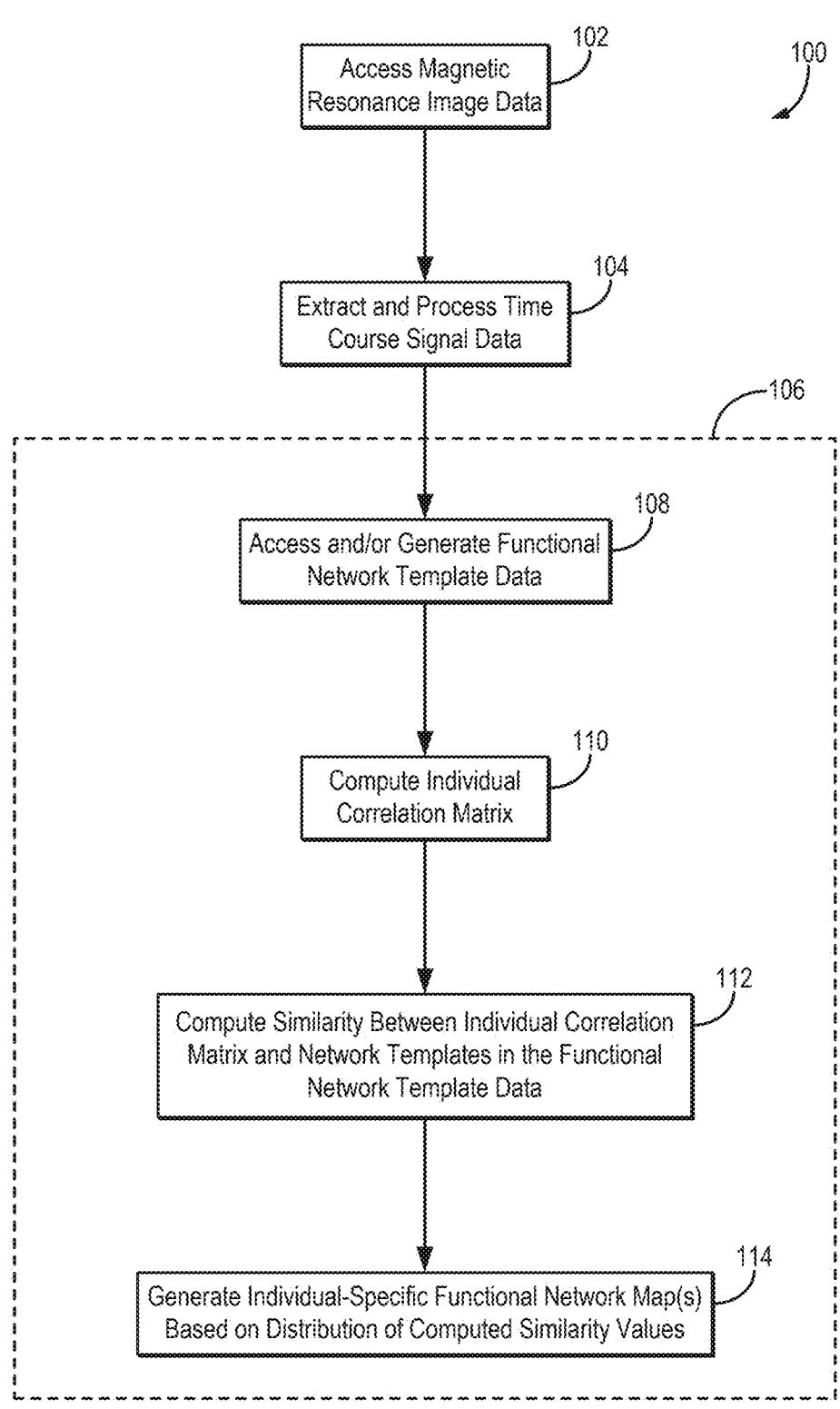
FIG. 1 is a flowchart setting forth the steps of an example method for generating an individual-specific functional network map using an overlapping template matching technique.

Described here are systems and methods for mapping functional networks for individuals and group populations based on magnetic resonance imaging, and using the resulting functional network maps (e.g., probabilistic maps of functional networks and/or integration zones where multiple functional networks overlap and/or interact) to guide or otherwise monitor the delivery of neuromodulation therapies, including non-invasive brain stimulation such as transcranial magnetic stimulation ("TMS"), transcranial direct current stimulation ("TCDS"), transcranial alternating current stimulation ("TCAS"), or the like. Additionally or alternatively, neuromodulation therapy can include other neurostimulations (e.g., deep brain stimulation), focused ultrasound-based neuromodulation, pharmacological-based neuromodulation, or the like.

Precision brain mapping of functional neural networks is a technique for examining individual network topography. Network topography across individuals appears to have some shared features, but the general shape and strength of connections remains highly individual-specific. It is an advantage of the systems and methods described in the present disclosure to generate probabilistic maps of functional networks from these individual-specific network maps, such that the community can use these probabilistic functional maps for targeted brain stimulation or other neuromodulation therapy delivery.

It is an advantage of the systems and methods described in the present disclosure to instead use precision brain mapping of functional neural networks for targeted brain stimulation or other neuromodulation therapy delivery. Additionally or alternatively, precision brain mapping can be used to monitor and/or measure the efficacy of targeted brain stimulation or other neuromodulation therapies, both on an individual treatment level and for group effects. In practice, collecting sufficient amounts of low-motion data in certain patient populations is either extremely challenging or not feasible. As described in the present disclosure, probabilistic maps based on precision mapping in a large cohort of individuals can instead be used such that any neural network of the brain can be targeted even in the absence of resting-state data from the participant receiving brain stimulation or other neuromodulation therapy. This technique can also be utilized for more invasive techniques for cortical stimulation and sub-cortical and cerebellar lead placements and stimulation.

There are many outpatient treatment centers for depression that use TMS, many of which use stereotactic neuronavigation. From a commercial perspective probabilistic maps can be used, for example, in a patient that is suffering from clinical depression, but has clinical contraindications for MRI scanning (e.g., aneurysm clips, claustrophobia, joint replacement, etc.). For those particular patients, it would be beneficial to have an external functional map that therapists could use to target a specific brain circuit. From a research perspective, using probabilistic maps for brain stimulation has many potential applications with respect to exploring brain function. The barrier to investigate functional neuroscience is often limited by access to an MRI (both logistically and financially). However, the financial barriers for investigators to acquire a TMS/TDCS/TACS stimulator are considerably less. Therefore, in instances where MRI scanning is not possible or inaccessible, researchers can benefit from the probabilistic maps generated from an external data set.

Referring now to FIG. 1, a flowchart is illustrated as setting forth the steps of an example method 100 for generating one or more individual-specific functional network maps from magnetic resonance image data using an overlapping template matching technique.

The method includes accessing magnetic resonance image data with a computer system, as indicated at step 102. Accessing the magnetic resonance image data can include retrieving previously acquired data from a memory or other data storage device or medium. Additionally or alternatively, accessing the magnetic resonance image data can include acquiring the data with a magnetic resonance imaging ("MRI") system and transferring or otherwise communicating the data to the computer system, which in some embodiments may be a part of the MRI system.

In general, the magnetic resonance image data include images acquired with an MRI system. The images can include a time-series of functional images acquired while a subject is performing a task (e.g., a functional task), while a subject is in a resting-state, or both. In these instances, the magnetic resonance image data includes task-based functional MRI data (e.g., data acquired while a subject is performing a functional task), resting-state functional MRI data, or both. As an example, a functional task may include a motor task (e.g., finger tapping), a monetary incentive delay task, a stop signal task, an emotional n-back task, and the like. The images can also include both anatomical images (e.g., T1-weighted images, T2-weighted images) and functional images.

A functional image depicts a region or volume of interest (e.g., a slice, slab, or volume) imaged within a subject's brain, and the time-series of functional images represents the time course of magnetic resonance signals in that region or volume over the duration of time during which the time-series of functional images was acquired. The time-varying magnetic resonance signals measured at a pixel or voxel location can be referred to as a time course, or time course signal data.

In some embodiments, time course signal data can be constructed by tracking the time-varying magnetic resonance signals measured at a grayordinate over the time-series of functional images. A grayordinate is a brainordinate within the gray matter of a subject's brain, and a brainordinate is a coordinate (e.g., a particular location) within a subject's brain. As one example, a brainordinate can be specified by a surface vertex, or node. As another example, a brainordinate can be specified by a volume voxel. Thus, a grayordinate corresponds to a particular location in the gray matter that can be specified as gray-matter surface vertices (e.g., cortical gray matter), gray-matter volume voxels (e.g., subcortical gray matter), or both.

In some embodiments, the magnetic resonance image data accessed with the computer system have been preprocessed (e.g., to denoise the images, the perform bias field correction, to perform brain extraction, to perform motion correction). In other embodiments, the magnetic resonance image data can be preprocessed using the computer system after accessing the data.

The time course signal data extracted from the magnetic resonance image data are then processed, as indicated at step 104. As one example, processing the time course signal data can include performing signal regression to detrend the time course signal data using one or more of mean whole brain, ventricle, and white matter signals, and additionally or alternatively one or more of displacement on the six degrees-of-freedom, rigid body registration, their derivatives, and their squares by regression. As another example, the time course signal data can be filtered using a bandpass filter. For example, a first order Butterworth bandpass filter can be used to filter signals between 9 MHz and 80 MHz backwards and forwards.

In some implementations, volumetric time course signal data (e.g., blood-oxygen-level-dependent ("BOLD") functional MRI volumetric data in the magnetic resonance image data) can be constrained to the cortical sheet. In these instances, the volumetric time course signal data are mapped to the cortical sheet, after which they are deformed and resampled to the original surface. The left and right surfaces can, in some instances, be combined with volumetric midbrain and hindbrain time course signal data into a CIFTI ("Connectivity Informatics Technology Initiative") format.

Additionally or alternatively, the time course signal data can be processed to correct for head motion of the subject. Head movement in the MRI scanner while the magnetic resonance image data are acquired interferes with the ability to identify a grayordinate from one time point to the next. In additional, the movement of a large electrically conductive tissue within the main magnetic field of the MRI scanner can introduce contaminating artifacts from eddy currents. To mitigate these effects, head motion can be controlled, or corrected for. As one non-limiting example, head motion can be corrected by using a framewise displacement threshold (e.g., of 0.2 mm) and only retaining time course signal data with at least 10 minutes of data post-motion correction.

Head movement can be calculated by framewise displacement ("FD") in mm as:

$$FD_i = |\Delta d_{ix}| + |\Delta d_{iy}| + |\Delta d_{iz}| + |\Delta\alpha_i| + |\Delta\beta_i| + |\Delta\gamma_i| \quad (1);$$

where $\Delta d_{ix}$ is the frame-to-frame change in the x-direction: $\Delta d_{ix} = d_{(i-1)x} - d_{ix}$, and so forth for the other rigid body parameters (i.e., changes along the y-direction $\Delta d_{iy}$ and z-direction $\Delta d_{iz}$, and changes along rotational directions $\alpha$, $\beta$, and $\gamma$). Rotational displacements can be converted from degrees to millimeters by calculating displacement on the surface of a sphere with a particular radium (e.g., a 50 mm radius, which is approximately the mean distance from the cerebral cortex to the center of the head). Frames can be removed from the time course signal data if their total relative movement in any direction (FD) is greater than a threshold (e.g., a 0.2 mm threshold) relative to the previous frame. Additionally or alternatively, frames can be removed from the time course signal data if they are contained within a segment of a number (e.g., 5) contiguous frames that violate the threshold.

Potential artifacts can be removed or otherwise mitigated based on a calculated standard deviation. For example, frames in the time course signal data that have outliers in the standard deviation of the BOLD signal can be removed, for example by using a median absolute deviation method.

One or more individual-specific functional networks maps are then generated from the time course signal data, as indicated at process block 106. The individual-specific functional networks maps are generated using an overlapping template matching technique.

Functional network template data for a plurality of different functional networks are accessed with the computer system, as indicated at step 108. Accessing the functional network template data can include retrieving previously generated data from a memory or other data storage device or medium. Additionally or alternatively, accessing the functional network template data can include generating the functional network template data with the computer system. Functional network templates can be generated from magnetic resonance image data (i.e., functional images and/or time course signal data) obtained from a group of subjects, or participants, as group-average network assignments in the brain (e.g., in the cortex).

The functional network template data can include templates for the following functional networks: the default mode network ("DMN"), the visual network ("VIS"), the frontal parietal network ("FPN"), the dorsal attention network ("DAN"), the ventral attention network ("VAN"), the salience network ("Sal"), the cingulo-opercular network ("CO"), the sensorimotor dorsal network ("SMd"), the sensorimotor lateral network ("SMl"), the auditory network ("AUD"), the temporal pole network ("Tpole"), the medial temporal network ("MTL"), the parietal occipital network ("PON"), and the parietal medial network ("PMN"). Sensory and motor systems can be combined due to the coupled nature of activation. In other implementations, the templates can include fewer of these functional networks and/or can include additional functional networks.

As a non-limiting example, functional network template data can be generated using an Infomap community detection algorithm. Brain network organization can be described using a two-level system of networks and nodes, respectively. Infomap is a network-describing algorithm based on the duality of finding community structure in networks and minimizing the description length of a random walk on a network. For example, the Infomap algorithm can minimize the number of bits (e.g., using Huffman coding) necessary to describe the whole network and using a random walk algorithm that uses connection weights to determine the minimum descriptor code length.

In some implementations, to ease the computational burden of processing a full set of connections as descriptors (which may include billions of such connections), the correlation matrix used in the Infomap algorithm can be thresholded to a percentage of the top connections (or edges).

Figure 2:
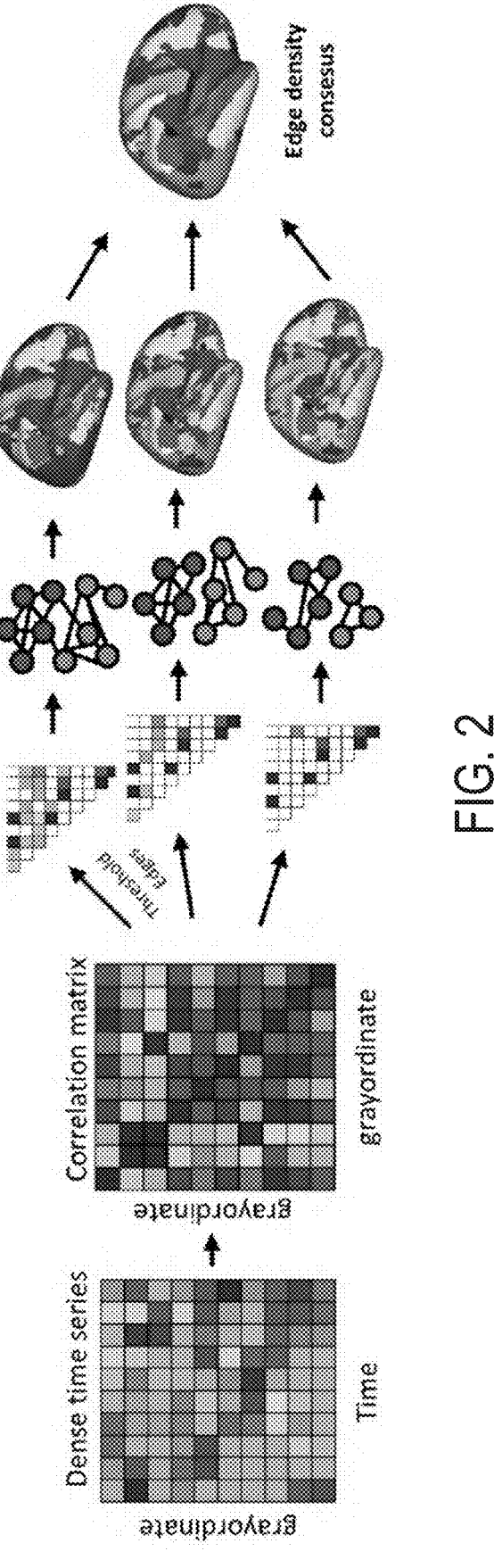
FIG. 2 illustrates an example implementation of an Infomap community detection algorithm for generating functional network template data.

FIG. 2 shows an example workflow for implementing an Infomap community detection algorithm to generate functional network template data. A correlation matrix is generated using motion-censored dense time series data. For example, a voxelwise correlation matrix can be computed by correlating the time course signal data (i.e., BOLD time series) at each grayordinate with the time course signal data of each other grayordinate. The correlation matrices for each participant in a group can be transformed and averaged across participants. For example, the correlation matrices can be transformed using a Fisher transform and the inverse Fisher transform can be applied to the group-average matrix.

The group-average matrix is then applied to the Infomap algorithm in order to identify functional networks across a range of edge density thresholds. For example, each upper triangle of the correlation matrix can be thresholded to various top percentages (e.g., 0.3, 0.4, 0.5, 1.0, 1.5, 2.0, 2.5, 3.0, 3.5, 4.0, 4.5, 5.0) of the connections. Those thresholded connections can then be used as the input for the Infomap algorithm. As noted above, Infomap uses a random walk to minimize bit-wise code length necessary to describe the whole system structure. The final network labels can be determined by generating a consensus across thresholds. In some embodiments, the Jaccard index of the spatial arrangement of grayordinates from the detected network can then be compared with those found in the group.

Additionally averaging can be applied. For example, the average time course signal of all grayordinates labeled for a particular network in the group-average consensus map can be extracted. The average time course signal can then be correlated with all other grayordinate time course signals in order to generate a network seedmap, which can be averaged across group participants. This can be repeated for each network, thereby generating a group-average functional network template map for each brain network.

For example, in some embodiments, an independent template is generated using a seed-based correlation (e.g., using an average time series correlated to all the grayordinates) for all networks. Seed-based correlations can be generated using a dense time series from each template participant that were smoothed with a within-frame spatial Gaussian smoothing kernel (e.g., with 2.55 mm smoothing) using each participant's own midthickness surfaces. The resulting networks can be converted to a CIFTI file format and applied to the smooth dense series to generate an average time series for each network. The time series of the seed can then be correlated with the times series of all other grayordinates. The seed and remaining time series can be motion censored using an FD of 0.2 mm (e.g., as described above, or using a different FD threshold) and outliers in the BOLD signal can be removed using the median absolute deviation in the remaining frames using the motion censoring method described above.

Seed-based correlation values can be averaged across all the participants in the template group, resulting in a vector of average correlation values for each network correlated with each grayordinate. Each network vector can be averaged independently across subjects in the template group to generate seed-based templates for each network. Each network template can then be thresholded (e.g., at $Z \geq 1$).

To generate precision maps for each participant, the whole-brain connectivity for each grayordinate can be analyzed by correlating the dense time series against all other grayordinates. For each participant in each test group, a Pearson or other correlation matrix can be generated for each connection using the dense time series. Time series can then be motion corrected to reduce artifacts induced by head motion, as described above.

Because connectivity matrices that are generated include subcortical brain regions, the correlation matrix can be Z-scored separately for each hemisphere, the subcortical region, and the connections between the cortex and the subcortex. This approach allows for normalization of connectivity between subcortex and cortex where there is the potential for a decreased signal-to-noise ratio ("SNR") in the subcortex. The whole-brain connectivity can be thresholded for each grayordinate to only include correlated grayordinates with Z-scores values greater than or equal to a threshold value (e.g., $Z \geq 1$). This results in a vector of whole-brain connectivity for each grayordinate that only includes grayordinates that are strongly correlated to a given network template.

Using the functional network template data, individual-specific network assignments are determined. A voxelwise correlation matrix is generated from the time course signal data, as indicated at step 110. For example, the correlation matrix can be generated by correlating the BOLD signals for each grayordinate with the BOLD signals every other grayordinate represented in the time course signal data. In some embodiments, the correlation matrix can be thresholded to a percentage of top connectivity values (e.g., the top 5% connectivity values) across grayordinates.

The similarity between the correlation matrix and one or more of the templates in the functional network template data is then computed, as indicated at step 112. As one example, An eta-squared ($\eta^2$) value, which is a measure of association or similarity at each grayordinate, can be calculated between the remaining grayordinates and each of the network templates. Alternatively, other similarity metrics can be computed, such as Dice coefficients.

Based on the similarity values, each grayordinate is assigned to one or more functional networks, generating output as one or more individual-specific functional network maps, as indicated at step 114. To generate overlapping networks for each participant, a data-driven approach is used to assign multiple networks to each grayordinate. For each network, the distribution of eta-squared values is plotted. The connectivity for each network demonstrates a characteristic skewed bimodal distribution. The distribution for eta-squared values can be distributed into a number of bins (e.g., 10,000 bins) and fitted with a cubic spline or other suitable spline, polynomial, or function. The distribution can then be smoothed (e.g., using a Savitzky-Golay filter using a 2,000 data point window). The local minimum of the bimodal distribution can be calculated by taking the derivative of the smoothed data between, for example, 4,000 and 7,000 bins. This local minimum can then be used as the threshold for whether or not a grayordinate is labelled with the particular network. For example, grayordinates above this threshold would receive the network assignment.

Figures 3A, 3B, 3C, 3D, 3E, 3F:
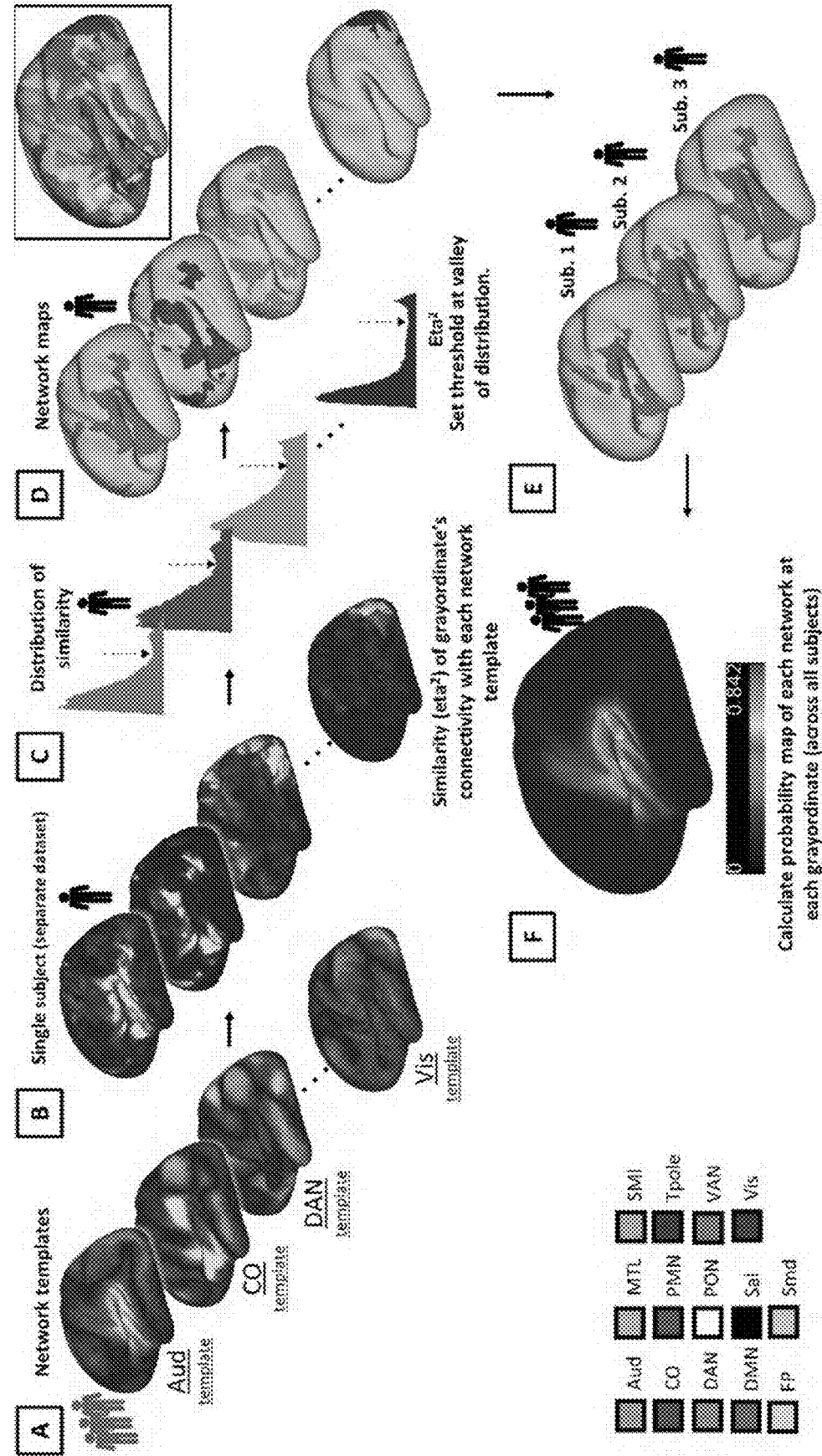
FIGS. 3A-3F illustrate an example implementation for generating individual-specific functional network maps for a group of subjects using an overlapping template matching technique, and generating a probabilistic functional network map therefrom.

FIG. 3 illustrates an example workflow for generating the individual-specific functional network maps using the overlapping template matching technique described in the present disclosure. A series of network templates (FIG. 3A) are accessed or otherwise generated. For each subject, the similarity at each grayordinate (using eta-squared or another suitable similarity metric) is calculated to each of the network templates shown in FIG. 3A (FIG. 3B). A threshold (dashed lines) for whether or not a grayordinate belongs to a network is set, based on the observed local minimum between peaks of bimodal distribution of eta-squared (FIG. 3C). Grayordinates that are above the threshold are then assigned that network label. All overlapping networks for an example subject are shown in the inset. After this procedure is performed for all subjects, a probabilistic map for each network (only the auditory network is shown for visualization purposes) can be calculated (as shown in FIG. 3E and FIG. 3F, and described below in more detail).

As indicated at step 116, after the individual-specific functional network maps are generated, they can be stored for later use, displayed to a user, or both. For example, the individual-specific functional network maps can be stored in a memory or other data storage device or medium using the computer system, where the individual-specific functional network maps can be later accessed for further processing or display to a user. In some embodiments, such as those described below, the individual-specific functional network maps can be stored and later accessed to generate a probabilistic functional network map, or atlas. Additionally or alternatively, the individual-specific functional network maps can be displayed to a user using the computer system.

As another example, the individual-specific functional network maps may be analyzed to monitor and/or measure the efficacy of targeted brain stimulation or other neuromodulation therapies that have been delivered or otherwise administered to the subject. For instance, the individual-specific functional network maps may be compared to reference or baseline maps to monitor and/or measure the efficacy of the targeted brain stimulation or other neuromodulation therapies. The comparison may be performed on a grayordinate basis, on a brainordinate basis, a network basis, or so on. For example, the individual-specific functional network map(s) generated for the subject can be compared with the reference or baseline to assess whether the topography (e.g., size, extent, brainordinate locations) or other characteristics or features of the subject's functional networks have changed in response to the targeted brain stimulation or other neuromodulation therapies.

As an example, each grayordinate or other brainordinate in the individual-specific functional network map can be compared with the reference functional network map to determine whether the functional network(s) associated with the selected brainordinate are different between the individual-specific functional network map and the reference functional network map. A difference may indicate that a grayordinate, or other brainordinate, that was previously not associated with a particular functional network is now associated with that functional network, indicating a positive response to the targeted brain stimulation or other neuromodulation therapy. In other examples, the comparison may be based on the strength of correlation of a grayordinate with a particular functional network. In these instances, an increase or decrease in the strength of correlation with a particular functional network can be indicative of a positive and/or negative response to the targeted brain stimulation or other neuromodulation therapy. The efficacy of the therapy can also be measured or monitored, for example, by correlating the change in the functional network(s) with a measure of treatment efficacy, whether at the individual-specific basis or relative to group effects.

As a non-limiting example, the reference or baseline map can include an individual-specific functional network map generated for the particular subject from a previous time point (e.g., before delivery of the targeted brain stimulation or other neuromodulation therapy). As another non-limiting example, a probabilistic functional network map (e.g., those described below) can be used as the reference or baseline. In these instances, the probabilistic functional network map may be generated for a group or population of individuals having a similar pre-treatment condition as the subject: a group or population of individuals having received a similar therapy, where the therapy has been observed as efficacious: a group or population of normal healthy individuals: or so on.

Figure 4:
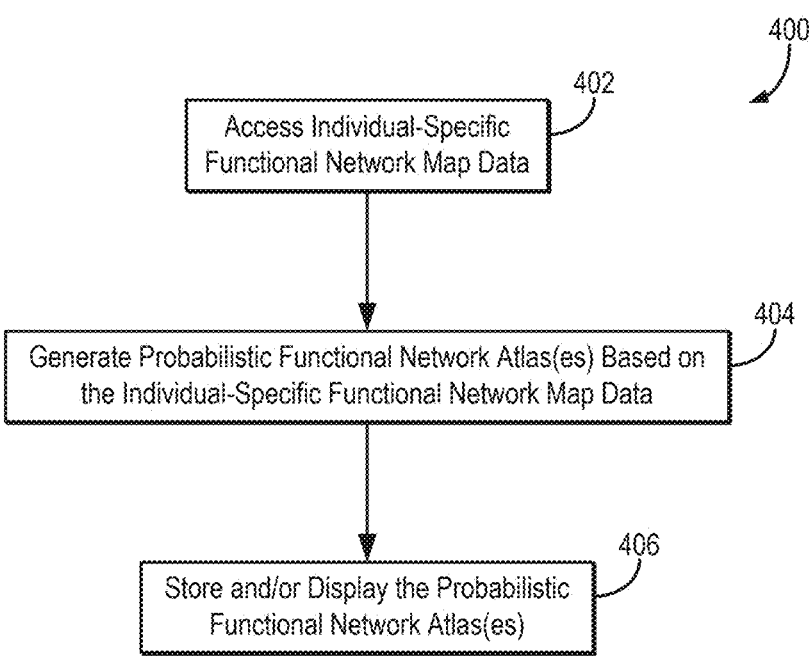
FIG. 4 is a flowchart setting forth the steps of an example method for generating a probabilistic functional network map, or atlas.

Referring now to FIG. 4, a flowchart is illustrated as setting forth the steps of an example method 400 for generating a probabilistic functional network map, or atlas, from individual-specific functional network maps obtained from a group of individuals.

The method includes accessing individual-specific functional network map data with a computer system, as indicated at step 402. Accessing the individual-specific functional network map data can include retrieving previously generated data from a memory or other data storage device or medium. Additionally or alternatively, accessing the individual-specific functional network map data can include generating the data with the computer system using a suitable method for generating individual-specific functional network maps.

As one example, the individual-specific network maps are generated (or have been generated) using an overlapping template matching method, such as using method 100 of FIG. 1. As another example, the individual-specific network maps are generated (or have been generated) using a template matching method. In a template matching method, grayordinates are assigned to the single functional network with the maximum eta-squared (or other similarity metric) value as opposed to assigning grayordinates to multiple different networks based in part on a distribution of the eta-squared (or other similarity metric) values. As still another example, the individual-specific network maps are generated (or have been generated) using an Infomap community detection method.

A probabilistic functional network map, or atlas, is generated from the individual-specific functional network map data, as indicated at process block 404. Probabilistic maps can be generated by calculating the probability that a grayordinate was assigned to a given network using all the participants within the group.

As one example, individual network assignments at each grayordinate are counted to calculate the total occurrence of a network being assigned to a particular grayordinate. Counting the grayordinates associated with different networks in this way produces a continuous probabilistic map for each network. The probabilistic maps indicate the probability of a given network being assigned at each grayordinate. In some embodiments, the frequency of network assignment values (or counts) can be divided by the number of individuals represented in the individual-specific functional network map data. The resulting ratios can be converted to percentage values to indicate the probability of a particular network being assigned to a particular grayordinate.

Thus, in some instances, each grayordinate in the probabilistic functional network atlas can indicate a probability (or percentage likelihood) that the selected grayordinate will be assigned to a particular network. For example, selecting a grayordinate in the probabilistic functional network atlas can return a sequence of probabilities (or percentage likelihoods) for multiple networks, such as {90.0% Aud, 8.5% CO, 1.4% DAN}. Additionally or alternatively, the probabilistic functional network atlas can indicate a population-based probability that grayordinates will be assigned to a particular network. An example of this is illustrated in FIG. 3F.

In some embodiments, the probabilistic functional network atlases can also be thresholded to enable visualization of network assignment probabilities at various probability thresholds. For example, thresholded probabilistic functional network atlases can indicate probability thresholds of grayordinates being assigned to particular functional networks in 50%, 55%, 60%, 65%, 70%, 75%, 80%, 85%, 90%, 95% of individuals or more. It will be appreciated that other percentage thresholds can also be used.

As indicated at step 406, after the probabilistic functional network atlases are generated, they can be stored for later use, displayed to a user, or both. For example, the probabilistic functional network atlases can be stored in a memory or other data storage device or medium using the computer system, where the probabilistic functional network atlases can be later accessed for further processing or display to a user. In some embodiments, such as those described below, the probabilistic functional network atlases can be stored and later accessed to guide and/or monitor the delivery of a neuromodulation therapy to a subject. Additionally or alternatively, the probabilistic functional network atlases can be displayed to a user using the computer system.

As another example, the probabilistic functional network maps, or atlases, may be analyzed to monitor and/or measure the efficacy of targeted brain stimulation or other neuromodulation therapies. For instance, the probabilistic functional network maps may be compared to reference or baseline maps to monitor and/or measure the efficacy of the targeted brain stimulation or other neuromodulation therapies. The comparison may be performed on a grayordinate basis, on a brainordinate basis, a network basis, or so on. For example, probabilistic functional network map(s) can be generated for a population or group of patients who have received a particular neuromodulation therapy for treating a particular condition. As a non-limiting example, the condition may be depression and the neuromodulation therapy may be a pharmacological neuromodulation therapy, such as the administration of an antidepressant at a certain dosage. The post-treatment probabilistic functional network map(s) can be compared with the reference or baseline map(s) to assess whether the topography (e.g., size, extent, brainordinate locations) or other characteristics or features of the functional networks have changed in response to the neuromodulation therapy. For example, the reference probabilistic functional network map(s) can be obtained from a group of healthy patients: a group of patients having the condition to be treated, but before treatment has been administered; and so on.

As an example, each grayordinate or other brainordinate in the post-treatment probabilistic functional network map(s) can be compared with reference probabilistic functional network map(s) to determine whether the functional network(s) associated with the selected brainordinate are different between the post-treatment and reference probabilistic functional network maps. A difference may indicate that the probability of a grayordinate, or other brainordinate, being associated with a particular functional network has changed between the reference and post-treatment conditions. In other examples, the comparison may be based on the strength of correlation of a grayordinate with a particular functional network, the probability of a grayordinate being associated with a particular functional network, and so on. In such instances, an increase or decrease in the strength of correlation with a particular functional network can be indicative of a positive and/or negative response to the targeted brain stimulation or other neuromodulation therapy. The efficacy of the therapy can also be measured or monitored, for example, by correlating the change in the functional network(s) with a measure of treatment efficacy (e.g., a clinical measure, a biomarker, etc.), whether at the individual-specific basis or relative to group effects.

These measured changes between the post-treatment group and the reference group can be used to monitor the efficacy of the neuromodulation therapy for treating the particular condition across a population or group of patients. In this way, the efficacy of new neuromodulation therapies can be evaluated. Additionally or alternatively, the efficacy of a neuromodulation therapy for treating a different condition can be evaluated. The measured changes can also identify specific brains regions where neuromodulation related effects on functional connectivity are observed. In this way, brain regions can be identified from the probabilistic functional network map(s), which can then be monitored in functional connectivity maps acquired from individual patients to evaluate whether the particular neuromodulation therapy is effective in those individual patients.

Most network connectivity studies to date assume that a given grayordinate participates in a single network. However, it has been suggested, and is likely, that some brain regions participate in multiple networks, or demonstrate nested or hierarchical structure that can be better described when allowing communities to overlap. For example, neurons that respond to multimodal stimuli likely participate in multiple networks. It is an advantage of the systems and methods described in the present disclosure that regions belonging to multiple communities can be identified by using the overlapping template matching procedure described above, which allows for networks to overlap.

As described above, the similarity of each grayordinate's BOLD signal to observed networks can be quantified by setting a data-driven threshold based on the observed local minima in the distribution of eta-squared values calculated for each network used in template matching. This technique allows for the detection of secondary and tertiary (and so forth) networks that communicate with a particular grayordinate that would otherwise be missed by only identifying the primary network.

Because the individual-specific functional network maps generated using the overlapping template matching technique described in the present disclosure can indicate the assignment of multiple different functional networks at any given grayordinate, these individual-specific functional network maps can be used to map or otherwise identify integration zones within individuals, or as a population probability. For example, by examining the overlapping networks for an individual, the number of networks observed at each grayordinate across the group can be averaged to examine the extent to which networks overlap in the population. Regions that demonstrate a high degree of overlap are thought to facilitate communication between networks.

Figure 5A:
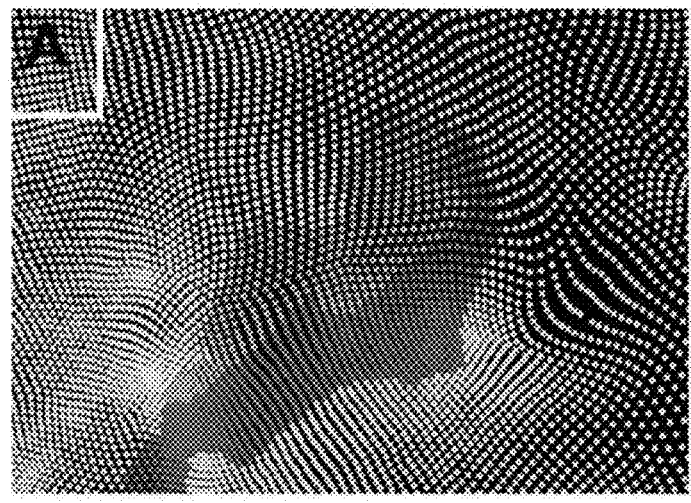
FIGS. 5A-5C illustrate examples of overlapping functional networks that can define integration zones.
Figure 5B:
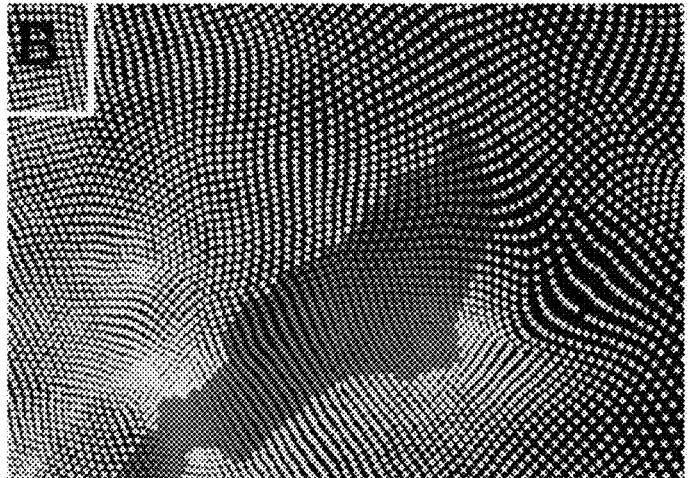
Figure 5C:
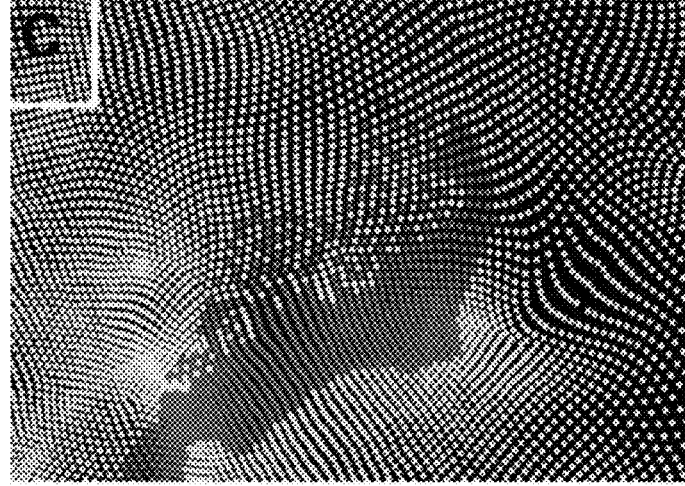

FIGS. 5A-5C illustrate example schema for how integration zones may arise from different topographical arrangements. White dots represent a functional unit (e.g. a neuron), the red and yellow regions represent separate functional networks, and the organ region (FIG. 5A) represents functional units that have shared properties of the red and yellow functional networks. In FIG. 5A, the functional units in orange participate in both the red and yellow networks. In FIG. 5B, functional units establish discrete borders between networks. In FIG. 5C, functional units participate in distinct networks, but are spatially interdigitated.

Due to their role in fundamental cognitive processes such as attention and consciousness, the core features of these integration zones are likely shared across the population and provide strong between-group reliability. Thus, individual-specific or probabilistic integration zone maps can be used to examine the mechanisms of information integration and relay, and also to guide targeted brain stimulation or other neuromodulation therapies.

Figure 6:
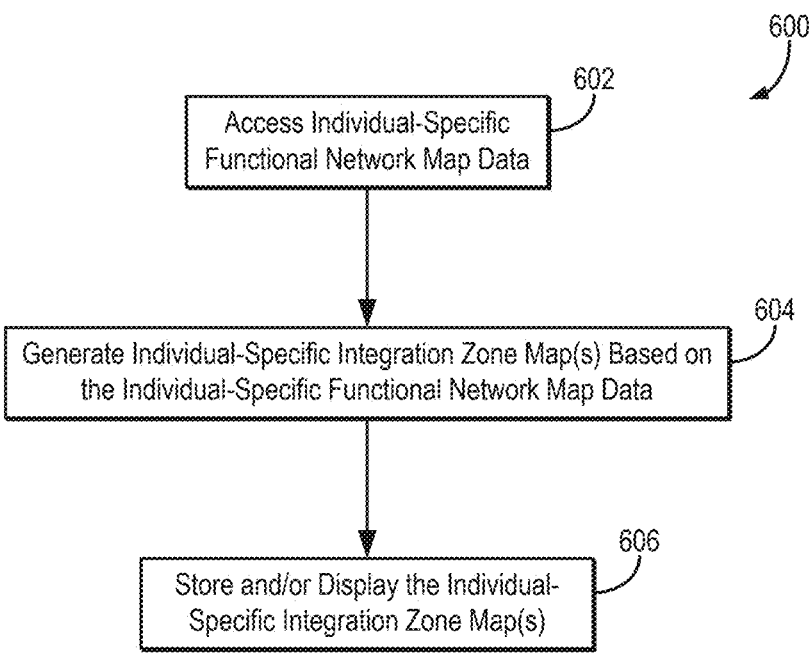
FIG. 6 is a flowchart setting forth the steps of an example method for generating an individual-specific integration zone map based on individual-specific functional network maps indicating overlapping functional networks at grayordinates.

Referring now to FIG. 6, a flowchart is illustrated as setting forth the steps of an example method 600 for generating an individual-specific integration zone map based on individual-specific functional network map data generated using an overlapping template matching technique (e.g., using method 100 of FIG. 1).

The method includes accessing individual-specific functional network map data with a computer system, as indicated at step 602. Accessing the individual-specific functional network map data can include retrieving previously generated individual-specific functional network map data from a memory or other data storage device or medium. Additionally or alternatively, accessing the individual-specific functional network map data can include generated the data with a computer system (e.g., by implemented method 100 of FIG. 1 using the computer system). As described above, the individual-specific functional network maps generated using an overlapping template matching technique indicate one or more functional network assignments for each grayordinate.

An individual-specific integration zone map can be generated based on the individual-specific functional network map data, as indicated at step 604. As one example, the number of functional network assignments at each grayordinate can be counted, and the counts of overlapping functional networks at each grayordinate can be stored as the individual-specific integration zone map. The count of networks at each grayordinate can define an integration zone.

Additionally or alternatively, the specific functional networks assigned to each grayordinate can also be stored for each grayordinate in the individual-specific integration zone map. In some embodiments, the number of networks and specific networks at each grayordinate can collectively define different integration zones. For example, clusters of grayordinates associated with overlapping functional networks can be identified and integration zones can be defined based on those identified clusters.

Figures 7A, 7B, 7C, 7D, 7E:
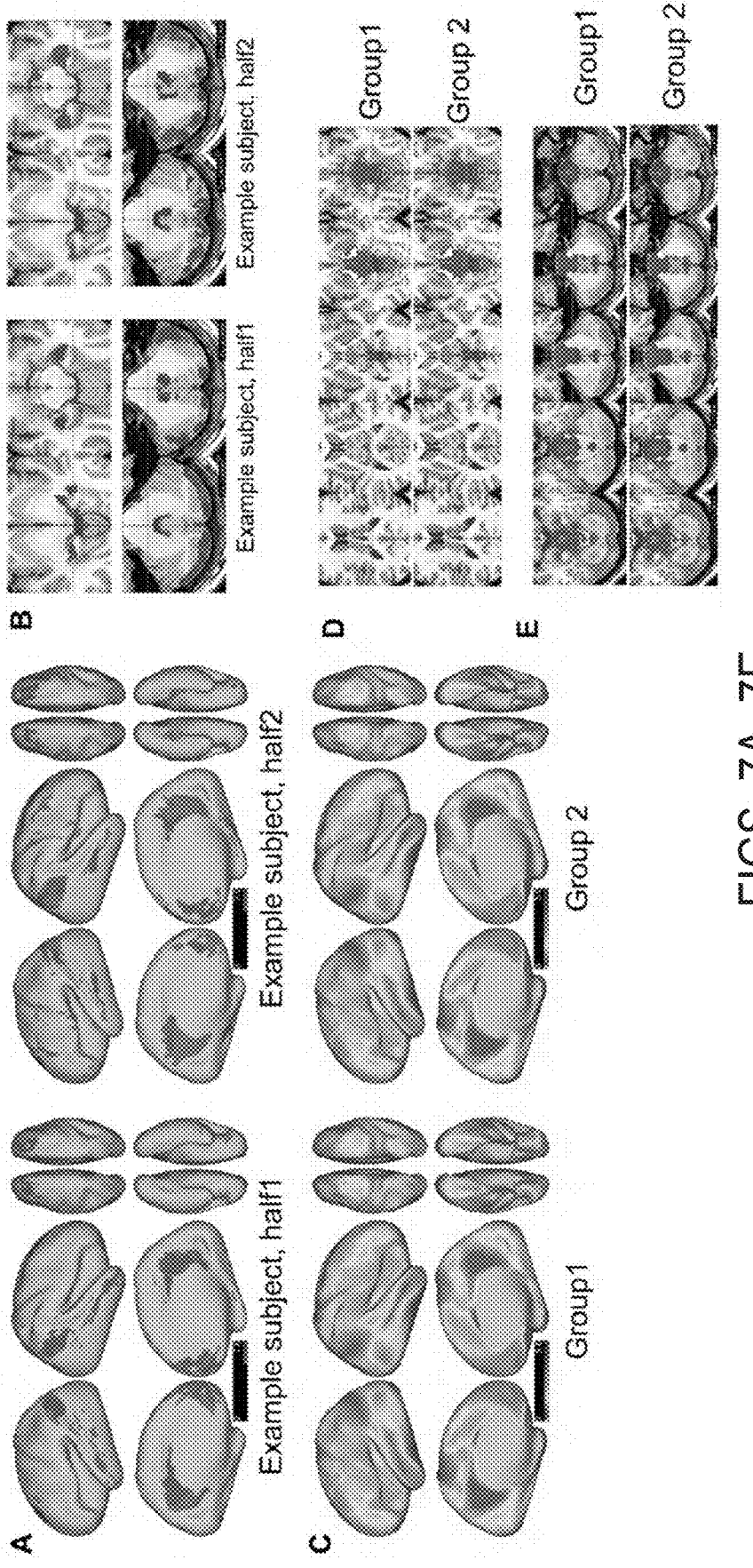
FIGS. 7A-7E show examples of identifying regions with multiple overlapping functional networks.

FIGS. 7A-7E illustrates an example where within a given subject, some integrative zones contain 8-10 networks converging in regions such as the posterior parietal cortex, precuneus, and posterior cerebellum, revealing a complex structure of internetwork communication. In this example, regions identified on the cortex (FIG. 7A), subcortical nuclei and cerebellum (FIG. 7B) that have five or more networks overlapping in an individual subject are shown. FIG. 7C-7E show the number of networks that overlap at each grayordinate for two different groups. FIG. 7C shows regions of the posterior cerebellum, in particular the spinocerebellum, that demonstrate high network overlap. FIG. 7D shows subcortical regions that demonstrate greater overlap of multiple networks, particularly the hippocampi.

As indicated at step 606, after the individual-specific integration zone maps are generated, they can be stored for later use, displayed to a user, or both. For example, the individual-specific integration zone maps can be stored in a memory or other data storage device or medium using the computer system, where the individual-specific integration zone maps can be later accessed for further processing or display to a user. In some embodiments, such as those described below, the individual-specific integration zone maps can be stored and later accessed to generate a probabilistic integration zone map, or atlas. Additionally or alternatively, the individual-specific integration zone maps can be stored and later accessed to guide or otherwise monitor the delivery of a neuromodulation therapy. Additionally or alternatively, the individual-specific integration zone maps can be displayed to a user using the computer system.

As another example, the individual-specific integration zone maps may be analyzed to monitor and/or measure the efficacy of targeted brain stimulation or other neuromodulation therapies that have been delivered or otherwise administered to the subject. For instance, the individual-specific integration zone maps may be compared to reference or baseline maps to monitor and/or measure the efficacy of the targeted brain stimulation or other neuromodulation therapies. The comparison may be performed on a grayordinate basis, on a brainordinate basis, or so on. For example, the individual-specific integration zone map(s) generated for the subject can be compared with the reference or baseline to assess whether the topography (e.g., size, extent, brainordinate locations, degree of overlap in functional networks, number of overlapping functional networks, etc.) or other characteristics or features of the subject's integration zones have changed in response to the targeted brain stimulation or other neuromodulation therapies.

As an example, each grayordinate or other brainordinate in the individual-specific integration zone map can be compared with the reference integration zone map to determine whether the functional network(s) associated with the selected brainordinate are different between the individual-specific integration zone map and the reference integration zone map. A difference may indicate that a grayordinate, or other brainordinate, that was previously not associated with a particular functional network is now associated with that functional network, indicating a positive response to the targeted brain stimulation or other neuromodulation therapy. Additionally or alternatively, a difference may also indicate that a grayordinate, or other brainordinate, is now associate with a different set of functional networks overlapping at the selected grayordinate, or other brainordinate. For instance, the difference may indicate that a first group of functional networks is overlapping at the grayordinate in the reference integration zone map and a second group of functional networks is overlapping at the grayordinate in the individual-specific integration zone map, where the first and second groups of functional networks differ by at least one functional network.

In other examples, the comparison may be based on the strength of correlation of a grayordinate with one or more functional networks. In these instances, an increase or decrease in the strength of correlation with one or more particular functional networks can be indicative of a positive and/or negative response to the targeted brain stimulation or other neuromodulation therapy. The efficacy of the therapy can also be measured or monitored, for example, by correlating the change in the functional network(s) with a measure of treatment efficacy, whether at the individual-specific basis or relative to group effects.

The efficacy of the therapy can be measured or monitored, for example, by correlating the change in the integration zone(s) with a measure of treatment efficacy, whether at the individual-specific basis or relative to group effects. For instance, a change (increase or decrease) in the number of functional networks overlapping in a certain region may be indicative of treatment efficacy, depending on the clinical outcome, such as by indicating beneficial neuroplasticity in response to the delivered treatment.

As a non-limiting example, the reference or baseline map can include an individual-specific integration zone map generated for the particular subject from a previous time point (e.g., before delivery of the targeted brain stimulation or other neuromodulation therapy). As another non-limiting example, a probabilistic integration zone map (e.g., those described below) can be used as the reference or baseline. In these instances, the probabilistic integration zone map may be generated for a group or population of individuals having a similar pre-treatment condition as the subject: a group or population of individuals having received a similar therapy, where the therapy has been observed as efficacious: a group or population of normal healthy individuals; or so on.

Figure 8:
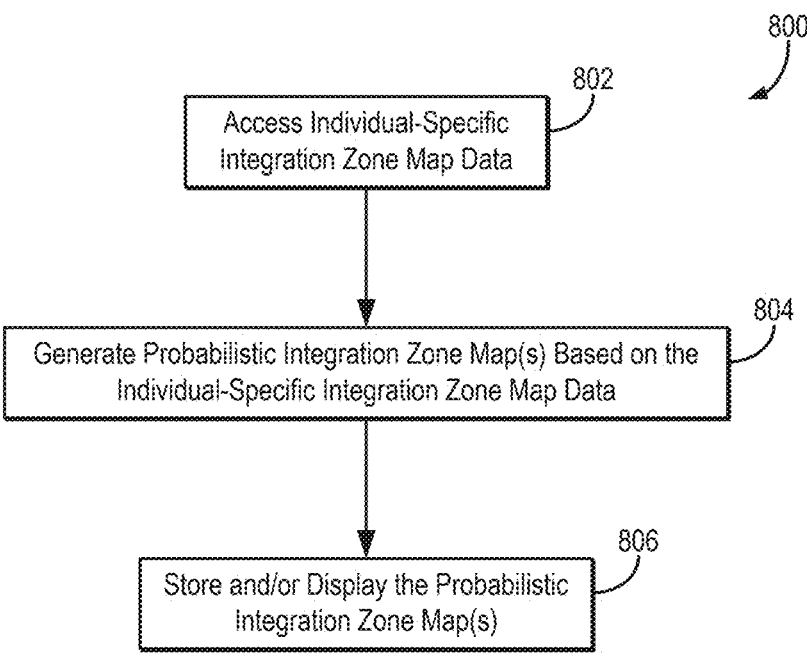
FIG. 8 is a flowchart setting forth the steps of an example method for generating a probabilistic integration zone map, or atlas.

Referring now to FIG. 8, a flowchart is illustrated as setting forth the steps of an example method 800 for generating a probabilistic functional network map, or atlas, from individual-specific functional network maps obtained from a group of individuals.

Figure 9:
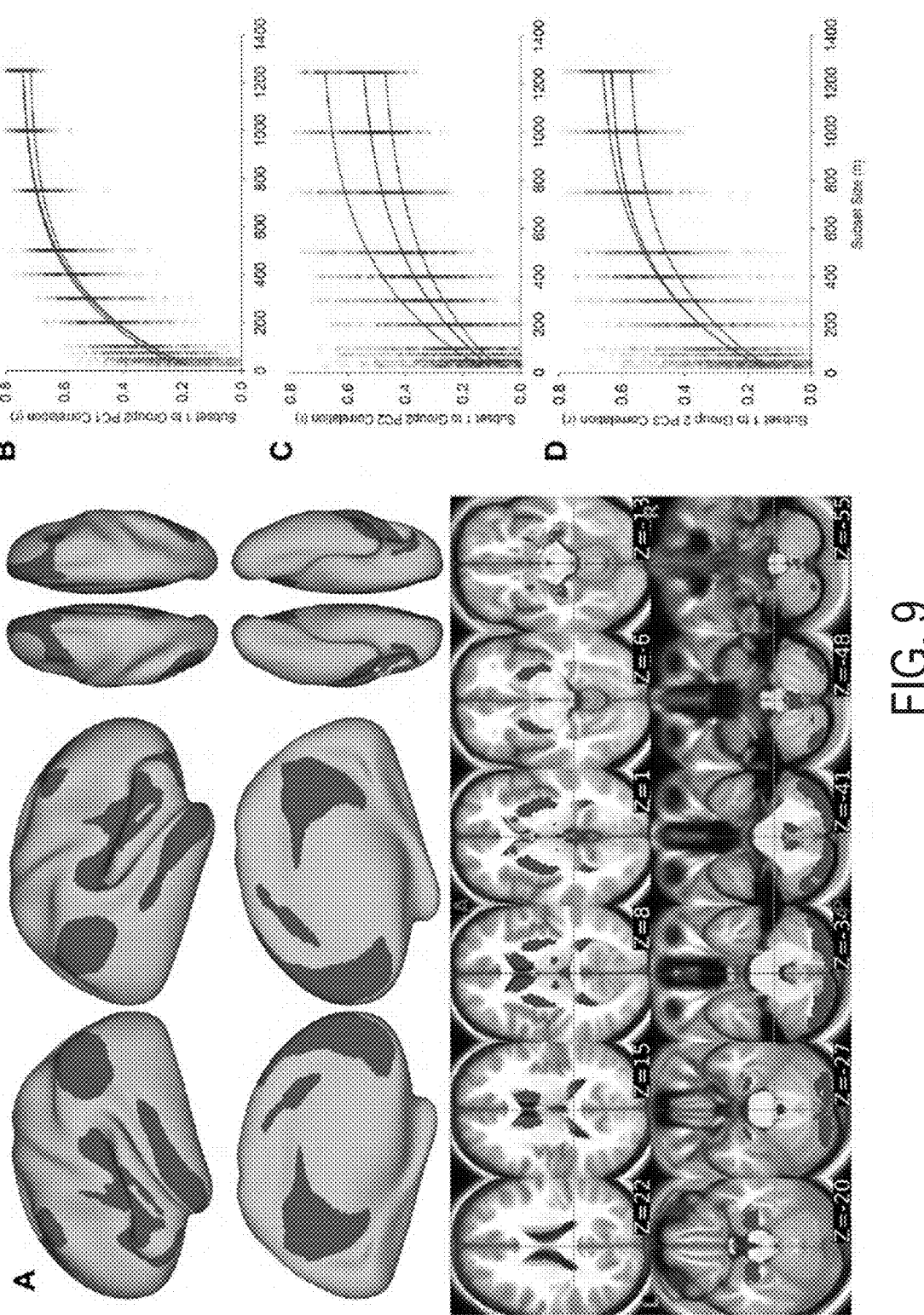
FIG. 9 shows an example of integration zones.

Integration zones across a population can be highly reliable. It is contemplates, for example, that regions with the highest number of networks closely resemble the default mode network, as shown in FIG. 9, including regions such as the parieto-occipital junction, middle temporal gyrus, posterior cingulate cortex/precuneus, hippocampus, and the posterior aspect of the posterior cerebellum. When integration zones are used to perform an identical subset reliability analysis using subsets of participants, it was observed that integration zones can provide more reproducible statistical maps of executive function brain-wide associations compared to using probabilistic functional network maps.

The method includes accessing individual-specific integration zone map data with a computer system, as indicated at step 802. Accessing the individual-specific integration zone map data can include retrieving previously generated data from a memory or other data storage device or medium. Additionally or alternatively, accessing the individual-specific integration zone map data can include generating the data with the computer system (e.g., using method 600 of FIG. 6).

A probabilistic integration zone map, or atlas, is generated from the individual-specific integration zone map data, as indicated at process block 804. As one example, probabilistic maps can be generated by calculating the probability that a grayordinate was assigned to more than one functional network, or that the grayordinate is associated with a cluster of grayordinates assigned to more than one functional networks (whether the same number or a different number of networks). As another example, probabilistic maps can be generated by calculating the probability that a grayordinate was assigned to two or more specific functional networks, or that a grayordinate is associated with a cluster of grayordinates assigned to those two or more functional networks.

Thus, in some instances, each grayordinate in the probabilistic integration zone atlas can indicate a probability (or percentage likelihood) that the selected grayordinate will be assigned to an integration zone, which may be a grayordinate assigned to more than one functional network (and/or clusters of grayordinates assigned to a similar number or different number networks), a grayordinate assigned to two or more specific functional networks (and/or clusters of grayordinates assigned to the same networks), and the like.

In some embodiments, the probabilistic integration zone atlases can also be thresholded to enable visualization of integration zone assignment probabilities at various probability thresholds. For example, thresholded probabilistic integration zone atlases can indicate probability thresholds of grayordinates being assigned to particular integration zones.

As indicated at step 806, after the probabilistic integration zone maps are generated, they can be stored for later use, displayed to a user, or both. For example, the probabilistic integration zone maps can be stored in a memory or other data storage device or medium using the computer system, where the probabilistic integration zone maps can be later accessed for further processing or display to a user. In some embodiments, such as those described below, the probabilistic integration zone maps can be stored and later accessed to guide or otherwise monitor the delivery of a neuromodulation therapy. Additionally or alternatively, the probabilistic integration zone maps can be displayed to a user using the computer system.

As another example, the probabilistic integration zone maps, or atlases, may be analyzed to monitor and/or measure the efficacy of targeted brain stimulation or other neuro-modulation therapies, similar to the probabilistic functional network maps. For instance, the probabilistic integration zone maps may be compared to reference or baseline maps to monitor and/or measure the efficacy of the targeted brain stimulation or other neuromodulation therapies. The comparison may be performed on a grayordinate basis, on a brainordinate basis, a network basis, integration zone basis, or so on. For example, probabilistic integration zone map(s) can be generated for a population or group of patients who have received a particular neuromodulation therapy for treating a particular condition. As a non-limiting example, the condition may be depression and the neuromodulation therapy may be a pharmacological neuromodulation therapy, such as the administration of an antidepressant at a certain dosage. The post-treatment probabilistic integration zone map(s) can be compared with the reference or baseline map(s) to assess whether the topography (e.g., size, extent, brainordinate locations, degree of overlap in functional networks, number of overlapping functional networks, etc.) or other characteristics or features of the integration zone(s) have changed in response to the neuromodulation therapy. For example, the reference probabilistic integration zone map(s) can be obtained from a group of healthy patients: a group of patients having the condition to be treated, but before treatment has been administered; and so on.

As an example, each grayordinate or other brainordinate in the post-treatment probabilistic integration zone map(s) can be compared with reference probabilistic integration zone map(s) to determine whether the functional network(s) and/or integration zone(s) associated with the selected brainordinate are different between the post-treatment and reference probabilistic integration zone maps. A difference may indicate that the probability of a grayordinate, or other brainordinate, being associated with one or more particular functional networks has changed between the reference and post-treatment conditions. Additionally or alternatively, a difference may indicate a different number of functional networks overlapping at the grayordinate. In other examples, the comparison may be based on the strength of correlation of a grayordinate with one or more particular functional networks, the probability of a grayordinate being associated with one or more particular functional networks, and so on. In such instances, an increase or decrease in the strength of correlation with one or more particular functional networks can be indicative of a positive and/or negative response to the targeted brain stimulation or other neuromodulation therapy. The efficacy of the therapy can also be measured or monitored, for example, by correlating the change in the functional network(s) with a measure of treatment efficacy (e.g., a clinical measure, a biomarker, etc.), whether at the individual-specific basis or relative to group effects.

These measured changes between the post-treatment group and the reference group can be used to monitor the efficacy of the neuromodulation therapy for treating the particular condition across a population or group of patients. In this way, the efficacy of new neuromodulation therapies can be evaluated. Additionally or alternatively, the efficacy of a neuromodulation therapy for treating a different condition can be evaluated. The measured changes can also identify specific brains regions where neuromodulation related effects on functional connectivity are observed. In this way, brain regions can be identified from the probabilistic integration zone map(s), which can then be monitored in functional connectivity maps acquired from individual patients to evaluate whether the particular neuromodulation therapy is effective in those individual patients.

Figure 12A:
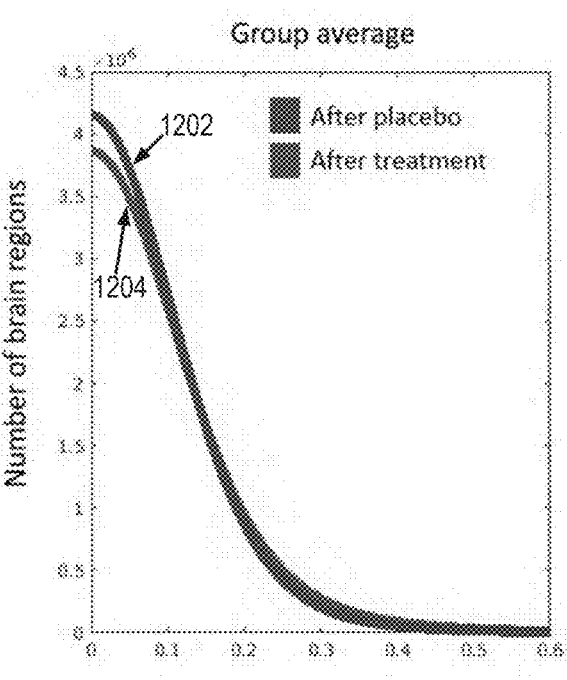
FIGS. 12A and 12B illustrate group average (FIG. 12A) and individual subject (FIG. 12B) differences in functional connectivity between medicated and unmedicated states.
Figure 12B:
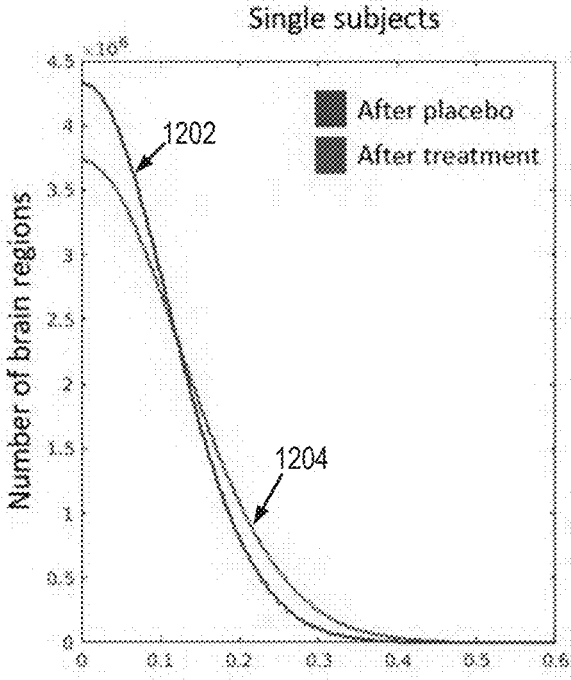

FIGS. 12A and 12B illustrate the relative abundance of difference in connectivity between fMRI scanning sessions at probabilistic regions in medicated participants 1202 and unmedicated participants 1204, which can be measured by comparing post-treatment and reference probabilistic integration zone maps and/or post-treatment and reference probabilistic functional network maps, as described above. FIG. 12A shows the average difference in the medicated (1202) participants and unmedicated (1204) participants, while FIG. 12B shows an individual difference in a subject while medicated (1202) and while unmedicated (1204). Monitoring changes in the brain due to medication have been elusive because of the variation in neural network topography. It is an advantage of the systems and methods described in the present disclosure that such changes in the brain due to pharmacological neuromodulation therapies can be monitored. The modulated regions, which show a high probability across the population of being in a given network, can provide the means to monitor changes in functional connectivity by comparing these changes to unmedicated changes.

Figures 10A, 10B, 10C, 10D, 10E, 10F:
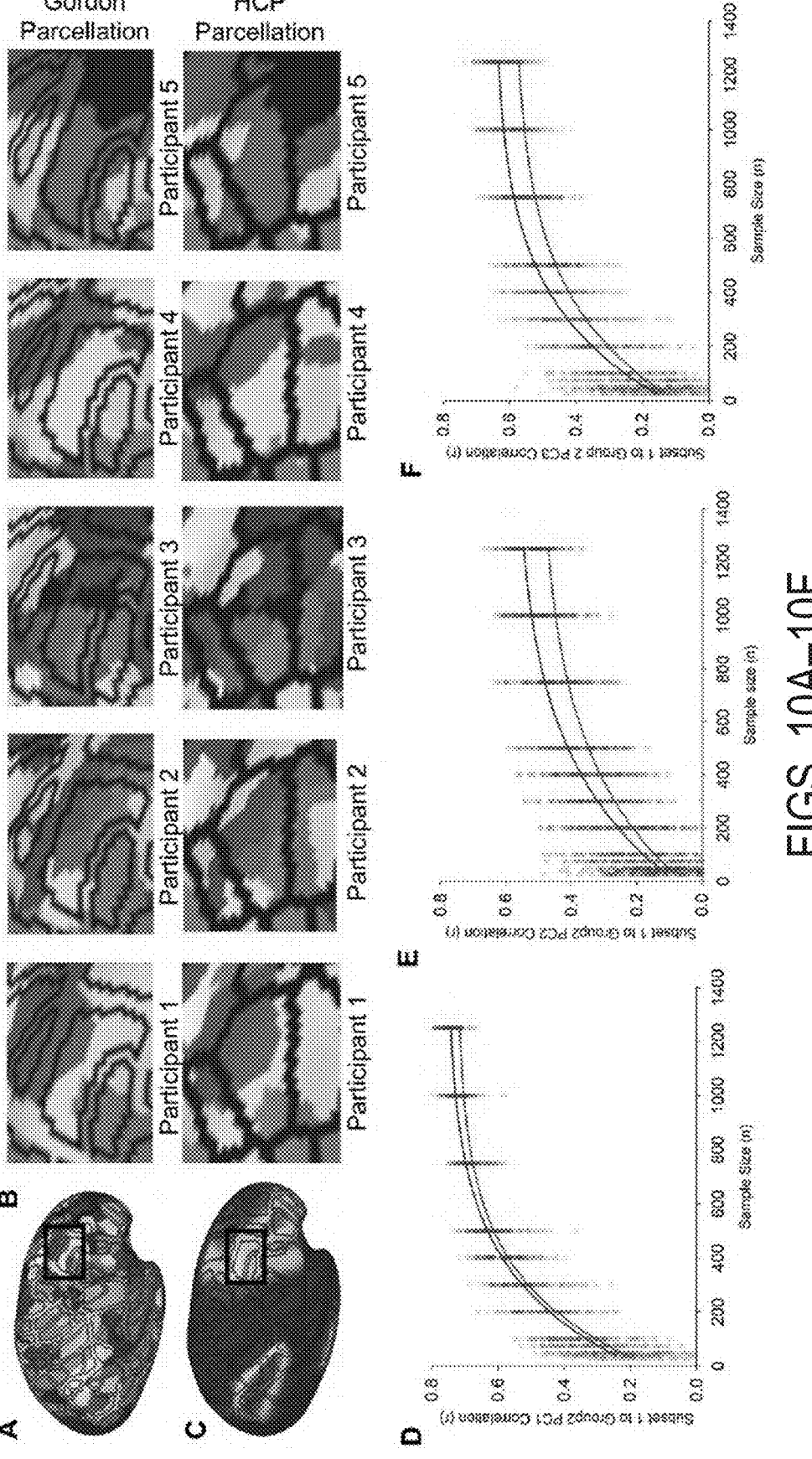
FIGS. 10A-10F show an example of functional networks having unique topographies that can confound conventional region-of-interest sets.

Structurally-informed parcellations, such as the Desikan parcellation, Destrieux parcellation, M-CRIB, and the Human connectome project ("HCP") atlas, derived from both myelin cytoarchitecture, cortical thickness, and task-based classification by computing the first derivative of each areal feature map, may not reflect underlying functional network communication. For example, FIGS. 10A-10F illustrate that neural networks have unique topographies that confound conventional ROI sets. FIG. 10A depicts how examination of the dorsolateral aspect of the frontal lobe demonstrates that for the ROIs shown, it may belong to one of several potential networks. FIG. 10B shows an example of an individual's whole brain neural networks with the Gordon Parcellation overlaid. FIG. 10C depicts a frontoparietal probabilistic map showing that grayordinates in this region do not consistently belong to this network (yellow), demonstrating inhomogeneity in network topography among the population. FIGS. 10D-10F show subset reliability analysis showing that using probabilistic functional network parcellation improves SNR in group-level predictions relative to the Gordon Parcellation. In these figures, blue circles indicate inter-group correlation for each random subset using the probabilistic functional network parcellation, and red circles indicate inter-group correlation for each random subset using the Gordon parcellation. Data were fitted with an exponential rise to maximum equation.

As shown in FIG. 10B, one disadvantage of the aforementioned structural parcellations is that they assume that a given parcel participates in the same network in all individuals (FIG. 10A). Individual-specific topography confounds this assumption about network assignments. Moreover, atlases that impose network assignments based on gyral-based neuroanatomy likely perpetuate the misconception that identical functions occur at identical locations across individuals, despite apparent inter-subject variation in both gyral anatomy and functional connectivity.

Analyses that assume identical network assignments across individuals based on structurally derived parcellations can therefore introduce two sources of noise: noise from the misalignment of structural parcellation-to-functional network and inter-subject network topographic variability. It is contemplated that behavioral prediction is improved when parcels from each network are reassigned based on individual-specific topography. By filtering out network topographies that are highly variable, inferences can be drawn based on commonly observed network locations. Advantageously, this limits the contribution of individual differences to support inferences about the group. The trade-off from this sparse brain coverage is that meaningful computations occur at these omitted variable locations where the brain has specifically allocated cortical real estate unique to the individual. These are the topographies that make individual brains function uniquely. Therefore, it may be that behaviors that are highly variable among different individuals originate from these locations that are the most spatially variable.

The probabilistic functional network atlas regions can provide predictive power about topographies associated with particular phenotypes. For example, in a group of typically developing children, if a voxel has a 90% chance of being in the default mode network, and in a separate group of children with autism, that voxel has a 90% chance of being labeled as the salience network, the probabilistic functional network atlas set provides a reference tool from which one can calculate probabilities of diagnosis based on topography.

Furthermore, the probabilistic functional network atlases provide a spatial reference for functional neuronavigation for targeted brain stimulation or other neuromodulation therapies. Historically, anatomical coordinates, landmarks, or the spatial location of task-based activations in fMRI, have been used to guide neuromodulation therapies, including non-invasive brain stimulation such as transcranial magnetic stimulation ("TMS"), transcranial direct current stimulation ("TCDS"), transcranial alternating current stimulation ("TCAS"), or the like. Additionally or alternatively, neuromodulation therapy can include other neurostimulations (e.g., deep brain stimulation), focused ultrasound-based neuromodulation, pharmacological-based neuromodulation, or the like.

Recent advances in brain stimulation using TMS have shifted focus from anatomical brain landmarks to functional brain networks with the goal of increasing treatment efficacy. Empirical evidence suggests that the effectiveness of the treatment not only depends on the spatial accuracy of the area to be stimulated, but also on the pattern of connectivity of such areas.

Figure 11A:
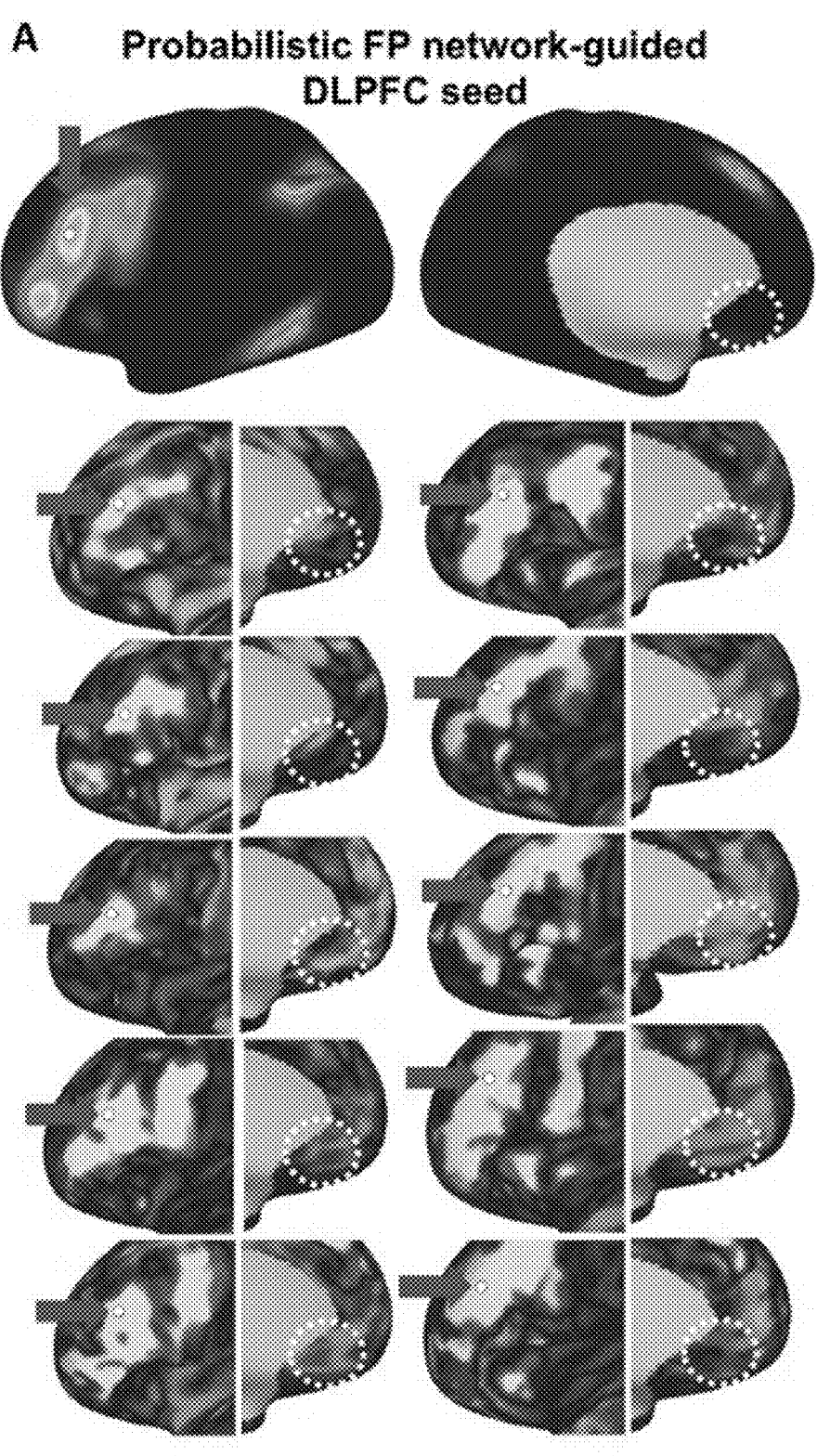
FIGS. 11A and 11B show probabilistic map-guided seed-based correlations for selecting target locations for neuromodulation.
Figure 11B:
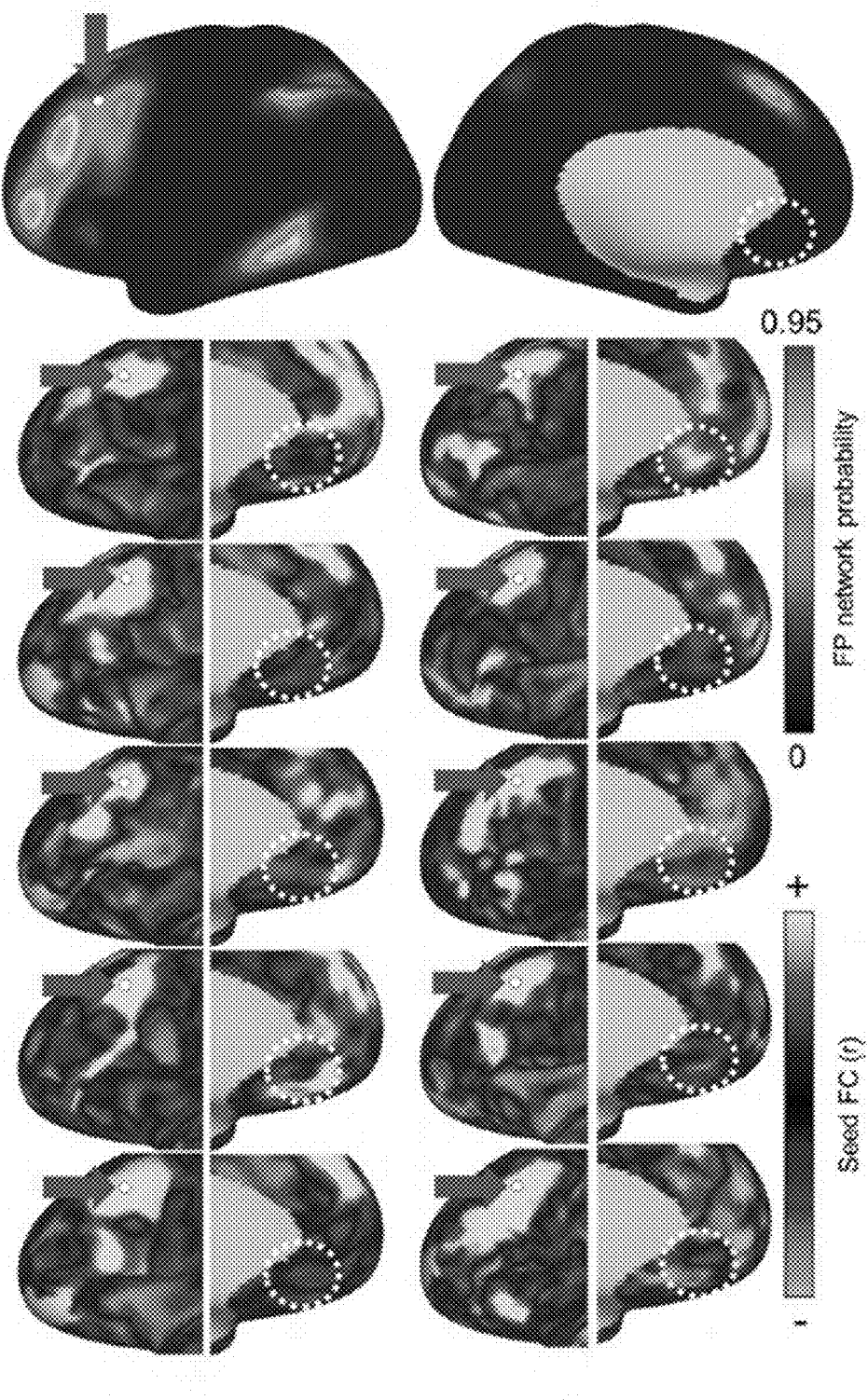

For example, in a recent study (R. F. H. Cash, et al., "Subgenual Functional Connectivity Predicts Antidepressant Treatment Response to Transcranial Magnetic Stimulation: Independent Validation and Evaluation of Personalization," *Biol. Psychiatry,* 2019; 86:e5-e7), it was observed that the variation in the dorsolateral prefrontal cortex ("DLPFC") (r)TMS stimulation site affects antidepressant response. Specifically, when rTMS stimulation was delivered at sites of the DLPFC that displayed a stronger negative correlation with the subgenual cortex, the antidepressant treatment showed better outcomes. Using a probabilistic functional network map of the frontoparietal network, a seed placed within a region of high network probability (0.75) within the DLPFC showed consistent anticorrelation with the subgenual cortex, as shown in FIG. 11A. However, when the seed was moved slightly outside of the region of high network consensus to a region with high network heterogeneity (0.35 probability), the correlation with the subgenual cortex was inconsistent, as shown in FIG. 11B. This suggests that the probabilistic functional network atlases allow for the quantification of the confidence of the spatial location of a network of interest, such that targets for therapeutic brain stimulation, or other neuromodulation, can be refined in situations where personalized network maps are not available.

Figure 13:
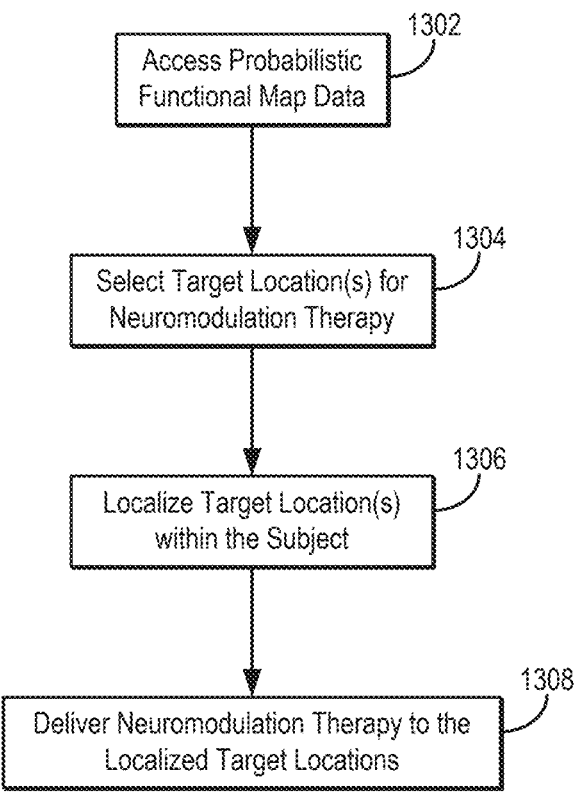
FIG. 13 is a flowchart setting for the steps of an example method for guiding neuromodulation delivery based on probabilistic functional map data (e.g., probabilistic functional network maps and/or probabilistic integration zone maps).

Referring now to FIG. 13, a flowchart is illustrated as setting forth the steps of a method 1300 for guiding or otherwise monitoring the delivery or administration of a neuromodulation therapy to a subject based on a probabilistic functional network atlas and/or a probabilistic integration zone map. Advantageously, using probabilistic functional mapping to guide and monitor neuromodulation therapy allows for treatment to be delivered to a subject without having to acquire extensive functional imaging data from the subject. That is, the method does not require any resting-state data from the subject. The method provides a measurable degree of confidence that the desired functional network is being targeted and provides potential targets for stimulation throughout the entire brain.

The method includes accessing a probabilistic functional map data with a computer system, as indicated at step 1302. Accessing the probabilistic functional map data can include retrieving previously generated data from a memory or other data storage device or medium. Additionally or alternatively, accessing the probabilistic functional map data can include generating the data with the computer system.

In some embodiments, the probabilistic functional map data can include a probabilistic functional network atlas, which may be a previously generated probabilistic functional network atlas retrieved from a memory or other data storage device or medium, or may be a probabilistic functional network atlas that is generated by the computer system (e.g., using method 400 of FIG. 4).

Additionally or alternatively, the probabilistic functional map data can include a probabilistic integration zone map, which may be a previously generated probabilistic integration zone map retrieved from a memory or other data storage device or medium, or may be a probabilistic integration zone map that is generated by the computer system (e.g., using method 800 of FIG. 8).

Based on the probabilistic functional map data, one or more target locations to which neuromodulation therapy will be delivered are selected using the computer system, as indicated at step 1304. The one or more target locations can be grayordinates or other brainordinates that are selected based on the condition for which neuromodulation therapy is being provided. For instance, in the example described above, the condition for treatment was depression, and the selected target location was a region of high network probability within the DLPFC, which showed consistent anticorrelation with the subgenual cortex. Additionally or alternatively, a target location can include a group or cluster of grayordinates, such as a group or cluster of grayordinates associated with a common functional network, two or more different functional networks, an integration zone, two or more integration zones, combinations thereof, or the like.

Thus, in general, selecting a target location for neuromodulation therapy can include determining a functional network, or networks, that when modulated by a neuromodulation therapy would provide a therapeutic effect to the subject (e.g., by controlling and/or improving the condition of the subject, or the like). As one example, target locations can be selected based on the condition to be treated. In some instances, selecting target locations can include selecting locations in the probabilistic functional network map data that have a probability of being assigned to a particular functional network that is above a certain threshold (e.g., 50%, 60%, 70%, 80%, 90%, etc.).

When the probabilistic functional map data include a probabilistic integration zone map, selecting the target location(s) can include selecting locations (e.g., grayordinates) associated with two or more particular functional networks that when modulated by a neuromodulation therapy would provide a therapeutic effect to the subject (e.g., by controlling and/or improving the condition of the subject, or the like). Additionally or alternatively, selecting the target location(s) can include selecting locations (e.g., grayordinates) in the probabilistic integration zone map corresponding to particular integration zones (e.g., regions where particular functional networks overlap or otherwise interact After the one or more target locations (e.g., grayordinates) to receive neuromodulation therapy are selected based on the probabilistic functional map data, the target locations are localized within the subject, as indicated at step 1306. For example, localizing the target locations can include identifying the target locations relative to the subject's anatomy, such that neuromodulation therapy can be delivered to the anatomical locations within the subject that correspond to the target locations selected relative to the probabilistic functional map data.

In a non-limiting example, the target locations can be localized within the subject by accessing medical image data of the subject using the computer system, where the medical image data include, for example, at least one anatomical image depicting the brain of the subject to whom neuromodulation treatment will be delivered. As an example, the medical image data may be anatomical magnetic resonance images of the subject. Accessing such magnetic resonance images can include retrieving previously acquired images from a memory or other data storage device or medium. Additionally or alternatively, accessing the magnetic resonance images can include acquiring the images with an MRI system and transferring or otherwise communicating the data to the computer system, which in some embodiments may be a part of the MRI system.

The medical image data and the probabilistic functional map data can then be coregistered, such that locations (e.g., grayordinates) in the probabilistic functional map data can be associated with anatomical locations within the subject. In this way, the target locations selected in the probabilistic functional map data can be localized relative to the subject's own anatomy.

Neuromodulation therapy is then delivered to the localized target location(s), as indicated at step 1306. For example, neuromodulation therapies such as TMS, TDCS, and/or TACS can be delivered transcranially to the localized target location(s) by positioning the neurostimulation device relative to the localized target locations. Similarly, neuromodulation therapies such as deep brain stimulation can be delivered by implanting an electrode adjacent the localized target locations, or otherwise directing electrical stimulation to the localized target locations.

In some embodiments, the neuromodulation delivered can be adjusted based on the particular localized target location. For example, if a localized target location corresponds to a grayordinate associated with an integration zone where multiple functional networks interact, a different neuromodulation may be delivered to that grayordinate than to a grayordinate associated with only a single functional network. In this way, the systems and methods described in the present disclosure can provide adaptive neuromodulation therapy that reduces or otherwise avoids modulating or overmodulating functional networks that may not provide a therapeutic effect to the subject.

Figure 14:
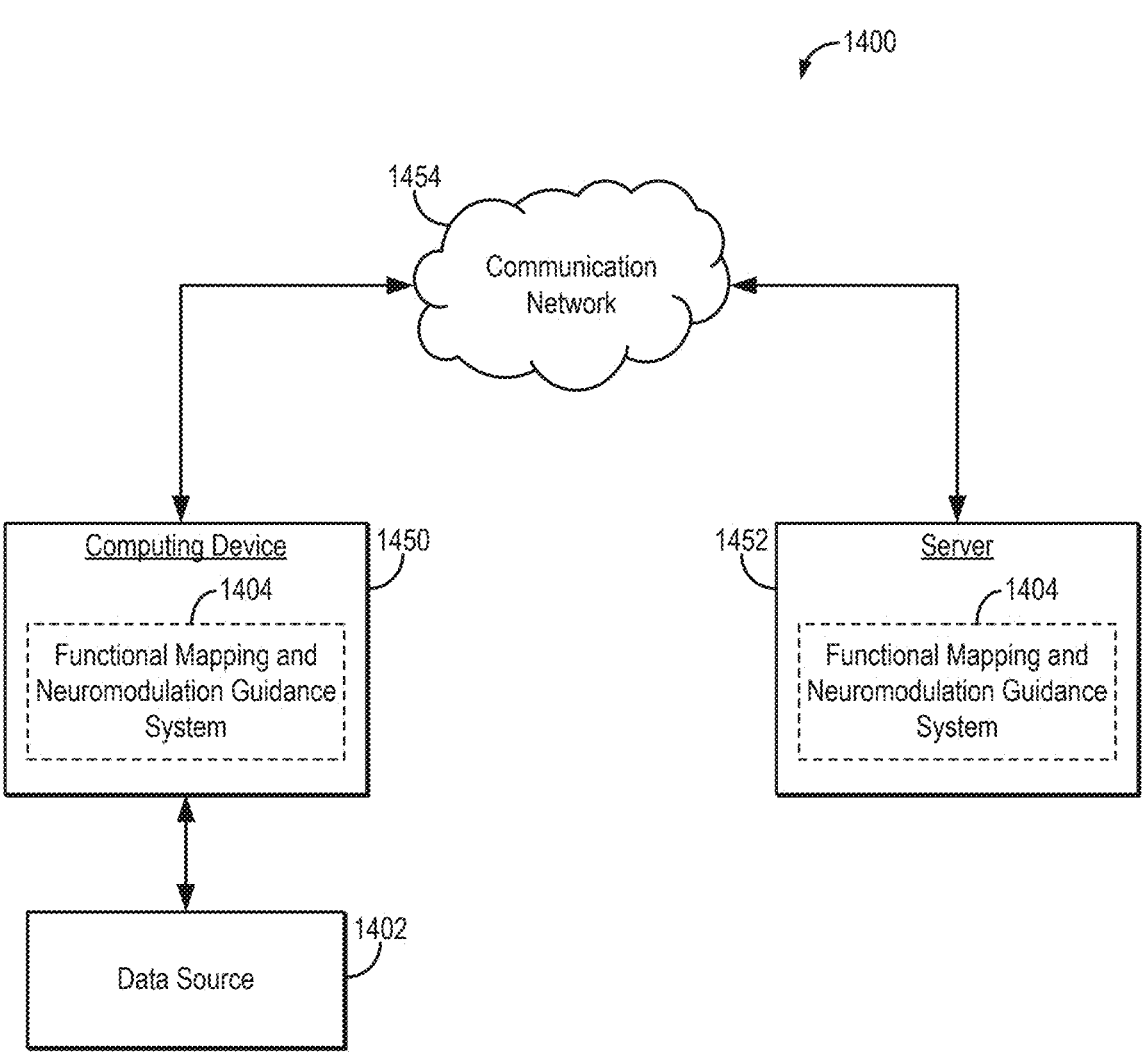
FIG. 14 is a block diagram of an example system for generating functional mapping data and performing neuromodulation guidance using the methods described in the present disclosure.

FIG. 14 shows an example of a system 1400 for generating functional mapping data and guiding neuromodulation therapy based on those data in accordance with some embodiments of the systems and methods described in the present disclosure. As shown in FIG. 14, a computing device 1450 can receive one or more types of data (e.g., magnetic resonance image data, time course signal data, individual-specific functional network/integration zone maps, probabilistic functional network/integration zone maps) from data source 1402, which may be a magnetic resonance image source. In some embodiments, computing device 1450 can execute at least a portion of a functional network mapping and neuromodulation guidance system 1404 to generate functional mapping data from data received from the data source 1402 and to guide the delivery of neuromodulation therapies based on those functional mapping data.

Additionally or alternatively, in some embodiments, the computing device 1450 can communicate information about data received from the data source 1402 to a server 1452 over a communication network 1454, which can execute at least a portion of the functional network mapping and neuromodulation guidance system. In such embodiments, the server 1452 can return information to the computing device 1450 (and/or any other suitable computing device) indicative of an output of the functional network mapping and neuromodulation guidance system.

In some embodiments, computing device 1450 and/or server 1452 can be any suitable computing device or combination of devices, such as a desktop computer, a laptop computer, a smartphone, a tablet computer, a wearable computer, a server computer, a virtual machine being executed by a physical computing device, and so on. The computing device 1450 and/or server 1452 can also reconstruct images from the data.

In some embodiments, data source 1402 can be any suitable source of image data (e.g., measurement data, images reconstructed from measurement data), such as an MRI system, another computing device (e.g., a server storing image data), and so on. In some embodiments, data source 1402 can be local to computing device 1450. For example, data source 1402 can be incorporated with computing device 1450 (e.g., computing device 1450 can be configured as part of a device for capturing, scanning, and/or storing images). As another example, data source 1402 can be connected to computing device 1450 by a cable, a direct wireless link, and so on. Additionally or alternatively, in some embodiments, data source 1402 can be located locally and/or remotely from computing device 1450, and can communicate data to computing device 1450 (and/or server 1452) via a communication network (e.g., communication network 1454).

In some embodiments, communication network 1454 can be any suitable communication network or combination of communication networks. For example, communication network 1454 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 1454 can be a local area network, a wide area network, a public network (e.g., the Internet), a private or semi-private network (e.g., a corporate or university intranet), any other suitable type of network, or any suitable combination of networks. Communications links shown in FIG. 14 can each be any suitable communications link or combination of communications links, such as wired links, fiber optic links, Wi-Fi links, Bluetooth links, cellular links, and so on.

Figure 15:
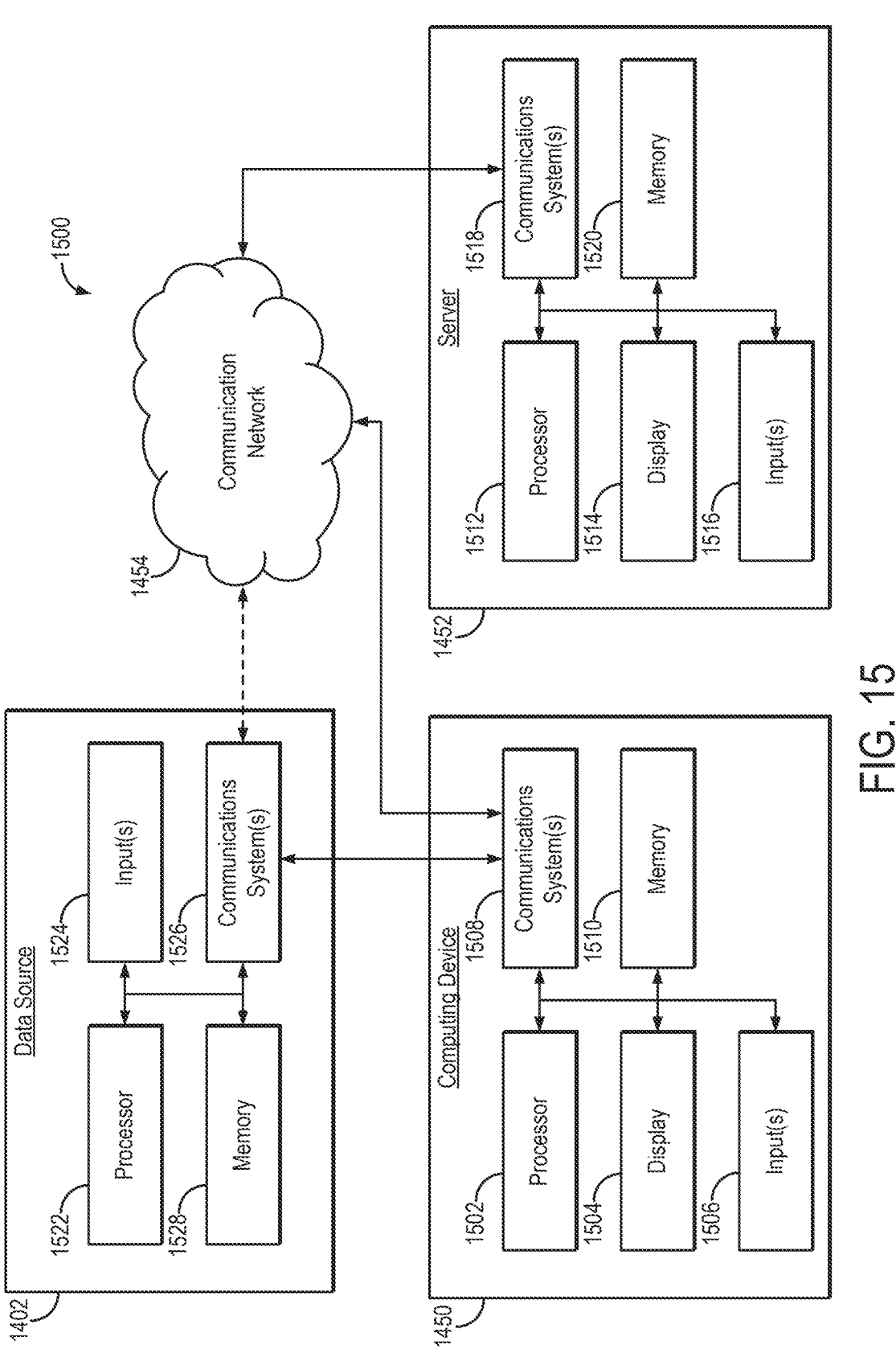
FIG. 15 is a block diagram of example components that can implement the system of FIG. 14.

Referring now to FIG. 15, an example of hardware 1500 that can be used to implement data source 1402, computing device 1450, and server 1452 in accordance with some embodiments of the systems and methods described in the present disclosure is shown. As shown in FIG. 15, in some embodiments, computing device 1450 can include a processor 1502, a display 1504, one or more inputs 1506, one or more communication systems 1508, and/or memory 1510. In some embodiments, processor 1502 can be any suitable hardware processor or combination of processors, such as a central processing unit ("CPU"), a graphics processing unit ("GPU"), and so on. In some embodiments, display 1504 can include any suitable display devices, such as a computer monitor, a touchscreen, a television, and so on. In some embodiments, inputs 1506 can include any suitable input devices and/or sensors that can be used to receive user input, such as a keyboard, a mouse, a touchscreen, a microphone, and so on.

In some embodiments, communications systems 1508 can include any suitable hardware, firmware, and/or software for communicating information over communication network 1454 and/or any other suitable communication networks. For example, communications systems 1508 can include one or more transceivers, one or more communication chips and/or chip sets, and so on. In a more particular example, communications systems 1508 can include hardware, firmware and/or software that can be used to establish a Wi-Fi connection, a Bluetooth connection, a cellular connection, an Ethernet connection, and so on.

In some embodiments, memory 1510 can include any suitable storage device or devices that can be used to store instructions, values, data, or the like, that can be used, for example, by processor 1502 to present content using display 1504, to communicate with server 1452 via communications system(s) 1508, and so on. Memory 1510 can include any suitable volatile memory, non-volatile memory, storage, or any suitable combination thereof. For example, memory 1510 can include RAM, ROM, EEPROM, one or more flash drives, one or more hard disks, one or more solid state drives, one or more optical drives, and so on. In some embodiments, memory 1510 can have encoded thereon, or otherwise stored therein, a computer program for controlling operation of computing device 1450. In such embodiments, processor 1502 can execute at least a portion of the computer program to present content (e.g., images, user interfaces, graphics, tables), receive content from server 1452, transmit information to server 1452, and so on.

In some embodiments, server 1452 can include a processor 1512, a display 1514, one or more inputs 1516, one or more communications systems 1518, and/or memory 1520. In some embodiments, processor 1512 can be any suitable hardware processor or combination of processors, such as a CPU, a GPU, and so on. In some embodiments, display 1514 can include any suitable display devices, such as a computer monitor, a touchscreen, a television, and so on. In some embodiments, inputs 1516 can include any suitable input devices and/or sensors that can be used to receive user input, such as a keyboard, a mouse, a touchscreen, a microphone, and so on.

In some embodiments, communications systems 1518 can include any suitable hardware, firmware, and/or software for communicating information over communication network 1454 and/or any other suitable communication networks. For example, communications systems 1518 can include one or more transceivers, one or more communication chips and/or chip sets, and so on. In a more particular example, communications systems 1518 can include hardware, firmware and/or software that can be used to establish a Wi-Fi connection, a Bluetooth connection, a cellular connection, an Ethernet connection, and so on.

In some embodiments, memory 1520 can include any suitable storage device or devices that can be used to store instructions, values, data, or the like, that can be used, for example, by processor 1512 to present content using display 1514, to communicate with one or more computing devices 1450, and so on. Memory 1520 can include any suitable volatile memory, non-volatile memory, storage, or any suitable combination thereof. For example, memory 1520 can include RAM, ROM, EEPROM, one or more flash drives, one or more hard disks, one or more solid state drives, one or more optical drives, and so on. In some embodiments, memory 1520 can have encoded thereon a server program for controlling operation of server 1452. In such embodiments, processor 1512 can execute at least a portion of the server program to transmit information and/or content (e.g., data, images, a user interface) to one or more computing devices 1450, receive information and/or content from one or more computing devices 1450, receive instructions from one or more devices (e.g., a personal computer, a laptop computer, a tablet computer, a smartphone), and so on.

In some embodiments, data source 1402 can include a processor 1522, one or more inputs 1524, one or more communications systems 1526, and/or memory 1528. In some embodiments, processor 1522 can be any suitable hardware processor or combination of processors, such as a CPU, a GPU, and so on. In some embodiments, the one or more inputs 1524 are generally configured to acquire data, images, or both, and can include an MRI system. Additionally or alternatively, in some embodiments, one or more inputs 1524 can include any suitable hardware, firmware, and/or software for coupling to and/or controlling operations of an MRI system. In some embodiments, one or more portions of the one or more inputs 1524 can be removable and/or replaceable.

Note that, although not shown, data source 1402 can include any suitable inputs and/or outputs. For example, data source 1402 can include input devices and/or sensors that can be used to receive user input, such as a keyboard, a mouse, a touchscreen, a microphone, a trackpad, a trackball, and so on. As another example, data source 1402 can include any suitable display devices, such as a computer monitor, a touchscreen, a television, etc., one or more speakers, and so on.

In some embodiments, communications systems 1526 can include any suitable hardware, firmware, and/or software for communicating information to computing device 1450 (and, in some embodiments, over communication network 1454 and/or any other suitable communication networks). For example, communications systems 1526 can include one or more transceivers, one or more communication chips and/or chip sets, and so on. In a more particular example, communications systems 1526 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 1528 can include any suitable storage device or devices that can be used to store instructions, values, data, or the like, that can be used, for example, by processor 1522 to control the one or more inputs 1524, and/or receive data from the one or more inputs 1524: to images from data: present content (e.g., images, a user interface) using a display: communicate with one or more computing devices 1450; and so on. Memory 1528 can include any suitable volatile memory, non-volatile memory, storage, or any suitable combination thereof. For example, memory 1528 can include RAM, ROM, EEPROM, one or more flash drives, one or more hard disks, one or more solid state drives, one or more optical drives, and so on. In some embodiments, memory 1528 can have encoded thereon, or otherwise stored therein, a program for controlling operation of data source 1402. In such embodiments, processor 1522 can execute at least a portion of the program to generate images, transmit information and/or content (e.g., data, images) to one or more computing devices 1450, receive information and/or content from one or more computing devices 1450, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a functional network map from functional magnetic resonance image data acquired from a subject using a magnetic resonance imaging (MRI) system, the method comprising:

(a) accessing functional magnetic resonance image data with a computer system, wherein the functional magnetic resonance image data comprise a time-series of images whose voxels depict blood-oxygen-level-dependent (BOLD) signals;

(b) forming time course signal data for each grayordinate with the computer system, wherein the time course signal data are formed for each gray ordinate as BOLD signals at the grayordinate measured over the time series of images;

(c) computing a correlation matrix from the time course signal data for each grayordinate using the computer system;

(d) accessing functional network template data with the computer system, wherein the functional network template data comprise functional network templates that are each indicative of grayordinates associated with a different functional network;

(e) computing similarity values between the correlation matrix and each functional network template in the functional network template data; and (f) generating an individual-specific functional network map with the computer system using a data-driven approach to assign multiple networks to at least one of the grayordinates based on the similarity values.

2. The method of claim 1, wherein the similarity values are eta-squared ($\eta^2$) values.

3. The method of claim 2, wherein generating the individual-specific functional network map with the computer system using the data-driven approach comprises:

generating a distribution of similarity values for each functional network;

computing a local minimum of the distribution for each functional network; and assigning grayordinates above the local minimum computed for a given functional network to that functional network.

4. The method of claim 3, wherein the local minimum of the distribution is computed as a derivative between a first bound of the distribution and a second bound of the distribution.

5. The method of claim 3, wherein the distribution is a bimodal distribution.

6. The method of claim 1, further comprising generating an individual-specific integration zone map with the computer system by determining the functional networks associated with each grayordinate in the individual-specific functional network map and assigning grayordinates in the individual-specific integration zone map to one or more integration zones based on the functional networks associated with each grayordinate.

7. The method of claim 6, wherein determining the functional networks associated with each grayordinate in the individual-specific functional network map comprises determining a number of functional networks assigned to each grayordinate.

8. The method of claim 6, wherein the functional magnetic resonance data were acquired after a neuromodulation therapy was delivered to the subject, and further comprising measuring an efficacy of the neuromodulation therapy by comparing the individual-specific integration zone map to a reference integration zone map.

9. The method of claim 8, wherein the neuromodulation therapy comprises a brain stimulation therapy.

10. The method of claim 9, wherein the brain stimulation therapy comprises one of transcranial direct-current stimulation, transcranial alternating-current stimulation, or transcranial magnetic stimulation.

11. The method of claim 8, wherein the neuromodulation therapy comprises a pharmacological-based neuromodulation therapy.

12. The method of claim 8, wherein measuring the efficacy of the neuromodulation therapy comprises comparing the individual-specific integration zone map to the reference integration zone map on a brainordinate basis.

13. The method of claim 12, wherein the individual-specific integration zone map is compared to the reference integration zone map on grayordinate basis.

14. The method of claim 8, wherein measuring the efficacy of the neuromodulation therapy comprises comparing the individual-specific integration zone map to the reference integration zone map on an integration zone basis.

15. The method of claim 8, wherein the reference integration zone map comprises a second individual-specific integration zone map generated for the subject before the neuromodulation therapy was delivered to the subject.

16. The method of claim 8, wherein the reference functional network map comprises a second individual-specific integration zone map generated for a different subject.

17. The method of claim 8, wherein the reference integration zone map comprises a probabilistic integration zone map associated with a group of subjects.

18. The method of claim 1, wherein the functional magnetic resonance data were acquired after a neuromodulation therapy was delivered to the subject, and further comprising measuring an efficacy of the neuromodulation therapy by comparing the individual-specific functional network map to a reference functional network map.

19. The method of claim 18, wherein the neuromodulation therapy comprises a brain stimulation therapy.

20. The method of claim 19, wherein the brain stimulation therapy comprises one of transcranial direct-current stimulation, transcranial alternating-current stimulation, or transcranial magnetic stimulation.

21. The method of claim 18, wherein measuring the efficacy of the neuromodulation therapy comprises comparing the individual-specific functional network map to the reference functional network map on a brainordinate basis.

22. The method of claim 21, wherein the individual-specific functional network map is compared to the reference functional network map on grayordinate basis.

23. The method of claim 18, wherein measuring the efficacy of the neuromodulation therapy comprises comparing the individual-specific functional network map to the reference functional network map on a functional network basis.

24. The method of claim 18, wherein the reference functional network map comprises a second individual-specific functional network map generated for the subject before the neuromodulation therapy was delivered to the subject.

25. The method of claim 18, wherein the reference functional network map comprises a second individual-specific functional network map generated for a different subject.

26. The method of claim 18, wherein the reference functional network map comprises a probabilistic functional network map associated with a group of subjects.

* * * * *